United States Patent

Driver et al.

[11] Patent Number: 5,116,960
[45] Date of Patent: May 26, 1992

[54] AMPHOTERICIN B DERIVATIVES

[75] Inventors: Michael J. Driver; David T. MacPherson; William S. MacLachlan, all of Epsom, England

[73] Assignee: Beecham Group p.l.c., Brentford, England

[21] Appl. No.: 367,390

[22] Filed: Jun. 9, 1989

[30] Foreign Application Priority Data

Jun. 13, 1988 [GB] United Kingdom ............... 8813927
Dec. 19, 1988 [GB] United Kingdom ............... 8829592

[51] Int. Cl.$^5$ .................... C07H 17/08; C07D 313/06
[52] U.S. Cl. ..................... 536/6.5; 549/269; 549/270
[58] Field of Search ............ 536/6.5; 514/31; 549/267, 269, 270

[56] References Cited

U.S. PATENT DOCUMENTS 3,945,993 3/1976 Schaffner et al. ................ 536/6.5

FOREIGN PATENT DOCUMENTS 1298172 11/1972 United Kingdom .

OTHER PUBLICATIONS

K. C. Nicolaou et al., "Retrosynthetic and Synthetic Chemistry on Amphotericin B . . . ", J. Chem. Soc., Chem. Commun., 1986.
Morrison et al, Organic Chemistry 3rd ed. (1979) p. 155.

Primary Examiner—Johnnie R. Brown
Assistant Examiner—Elli Peselev
Attorney, Agent, or Firm—Hopgood, Calimafde, Kalil, Blaustein & Judlowe

[57] ABSTRACT

Compounds of formula (I) or salts thereof:

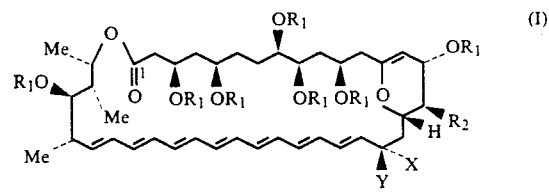

wherein:
each $R_1$ is independently hydrogen or a silyl protecting group; $R_2$ is a carboxylic acid or derivative thereof; a ketone or aldehyde function; hydroxymethyl in which the hydroxyl function is optionally silylated, or substituted by hydroxy $C_{1-4}$ alkyl, alkoxy $C_{1-4}$ alkyl, alkoxycarbonyl $C_{1-4}$ alkyl, hydroxycarbonyl $C_{1-4}$ alkyl, alkyl, alkanoyl, or optionally substituted aryl or aroyl; one of X and Y is hydrogen, and the other is a sugar residue; hydroxy; optionally substituted $C_{1-6}$ alkoxy or $C_{3-8}$ cycloalkoxy; alkanoyloxy; thioalkanoyloxy; sulphonyloxy; halogen; or optionally substituted aryloxy, aralkyloxy or aroyloxy; or X and Y together with the carbon atom to which they are bonded are a carbonyl group or derivative thereof, are provided; their use as chemical intermediates and in the treatment of fungal infections is described.

9 Claims, No Drawings

AMPHOTERICIN B DERIVATIVES

The present invention relates to novel compounds, their preparation, their use as chemical intermediates and in the treatment of fungal infections in animals, including humans.

The polyene macrolide amphotericin B, produced by *Streptomyces nodosus*, is widely used for the treatment of fungal infections.

Amphotericin B is the only complex polyene macrolide whose molecular structure and absolute configuration has been firmly established by X-ray crystallographic analysis. Amphotericin B has the formula (A):

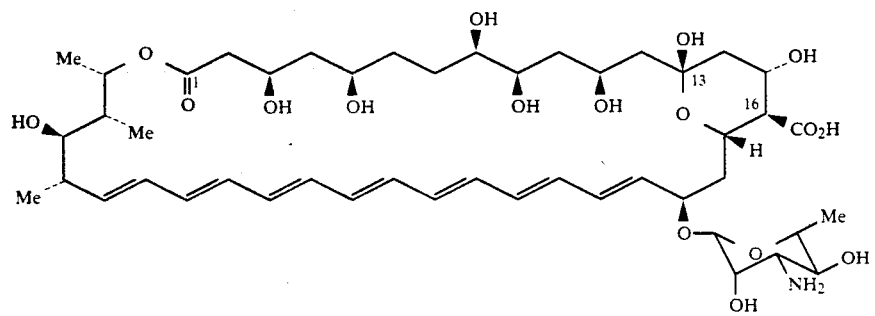

Derivatives of amphotericin B are reported in the literature. Nicolaou et al. (J. Chem. Soc. Chem. Commun., 413, (1986)) describe acetylation of the amine function and methylation of the carboxylic acid function of amphotericin B to afford the acetamide methyl ester derivative of formula (B):

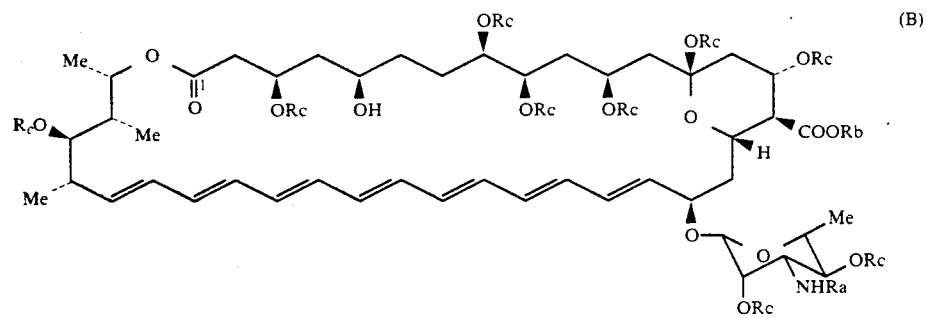

wherein $R_a$ is acetyl, $R_b$ is methyl and $R_c$ is hydrogen. Persilylation of the above-mentioned derivative using trimethylsilyl trifluoromethanesulphonate with 2,6-lutidine at 0° C. is reported by Nicolaou et al. (J. Chem. Soc. Chem. Commun., 686, (1987)) to give the compound of formula (B) in which $R_a$ is acetyl, $R_b$ is methyl and $R_c$ is trimethylsilyl.

Exposure of the above-mentioned persilyl derivative to N-bromosuccinimide in carbon tetrachloride at 25° C. is reported, in the same paper, to give the corresponding aglycone derivative and, on reduction with sodium borohydride in methanol at 0° C., the corresponding silylated amphoterenolide B methyl ester.

Analogous silylation reactions have now been carried out which provide novel derivatives of amphotericin B in which the labile hydroxyl group at the anomeric 13-position is eliminated. The 13,14-double bond, so formed, is retained during subsequent deglycosidation reactions. The 19-carbonyl function of the resulting aglycone derivative may be reduced to provide the corresponding amphoterenolide, in which the 19-hydroxyl function may be further derivatised.

The novel 13-ene derivatives are useful as intermediates in the preparation of purified amphotericin B and derivatives thereof. Certain of the novel 13-ene derivatives are themselves pharmaceutically active and have potential utility as anti-fungal agents.

13-Ene derivatives provide an effective form of protection for the labile 13-hydroxyl group of amphotericin B and its derivatives, which may be regenerated and/or further derivatised as required.

The labile nature of the 13-hydroxyl group frequently gives rise to unwanted by-products during chemical reactions on amphotericin B and its derivatives. Elimination of the 13-hydroxy group prevents the formation of such by-products. 13-Ene compounds may thus be utilised to enhance both purity and yield during chemical manipulation of amphotericin B and its derivatives.

Furthermore, the 13-, 14- and 15- positions may be selectively functionalised, selective functionalisation at the 15-position being facilitated by allylic activation.

Accordingly, the present invention provides a compound of formula (I), or a salt thereof:

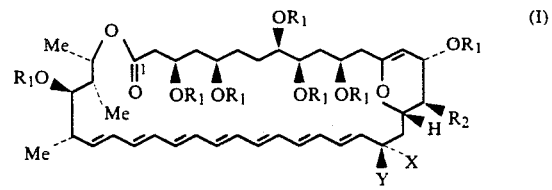

wherein:
  each $R_1$ is independently hydrogen or a silyl protecting group; $R_2$ is a carboxylic group or derivative thereof; a ketone or aldehyde function; hydroxymethyl in which the hydroxyl function is optionally silylated, or substituted by hydroxy $C_{1-4}$ alkyl, alkoxy $C_{1-4}$ alkyl, alkoxycarbonyl $C_{1-4}$ alkyl, hydroxycarbonyl $C_{1-4}$ alkyl, alkyl, alkanoyl, or optionally substituted aryl or aroyl; one of X and Y is hydrogen, and the other is a sugar residue; hydroxy; optionally substituted $C_{1-6}$ alkoxy or $C_{3-8}$ cycloalkoxy; alkanoyloxy; thioalkanoyloxy; sulphonyloxy; halogen; or optionally substituted aryloxy, aralkyloxy or aroyloxy; or X and Y together with the carbon atom to which they are bonded are a carbonyl group or derivative thereof; with the proviso that when each $R_1$ is trimethylsilyl and $R_2$ is methoxycarbonyl, one of X and Y is not hydroxy, 4-nitro-phenylcarboxy or N-acetyl-3,4-O-trimethylsilyl-mycosamine, or X and Y together with the carbon atom to which they are bonded are not a carbonyl group; when each $R_1$ is hydrogen and $R_2$ is methoxycarbonyl, one of X and Y is not hydroxy or 4-nitro-phenylcarboxy; and when each $R_1$ is hydrogen and $R_2$ is carboxy, one of X and Y is not hydroxy.

Unless otherwise specified, each alkyl group is preferably a $C_{1-8}$ group, more preferably a $C_{1-6}$ group and may be straight chain or branched. Optional substitutents at any carbon atom of an alkoxy or $C_{3-8}$ cycloalkoxy group include carboxy, alkoxycarbonyl, hydroxy, halogen, alkyl, alkoxy, and amino optionally substituted by $C_{1-6}$ alkyl. The term halogen includes fluorine, chlorine, bromine and iodine.

The term carboxylic acid derivative includes ester, thioester, amide, anhydride and acid halide. Esters and thioesters include alkoxycarbonyl, aryloxycarbonyl, heteroaryloxycarbonyl, alkylthiocarbonyl, arylthiocarbonyl and heteroarylthiocarbonyl groups. Amides include primary, secondary and tertiary amides. For example the amine moiety may be substituted by one or two alkyl groups. The term ketone includes both alkyl, aryl and heteroaryl ketones.

The term sulphonyloxy includes alkyl derivatives such as mesylate and aryl derivatives such as tosylate. The term carbonyl group derivative includes oxime and hydrazone.

The term aryl includes both monocyclic and bicyclic carbocylic moieties, for example phenyl and naphthyl. An aryl moiety may be mono-, di-, or tri-substituted by groups including carboxy, alkoxycarbonyl, hydroxy, alkyl, alkoxy, halogen, and amino optionally substituted by alkyl, and is preferably mono- or di-substituted.

The term heteroaryl includes 5- or 6- membered monocyclic and 9- or 10- membered bicyclic heteroaryl.

In addition, 5- or 6- membered monocyclic and 9- or 10-membered bicyclic heteroaryl preferably contain one or two heteroatoms selected from nitrogen, oxygen and sulphur which in the case of there being more than one heteroatom may be the same or different. When 9- or 10-membered bicyclic heteroaryl, the two rings are preferably fused with one 5- or 6- membered ring containing a single heteroatom.

Compounds of formula (I) and salts thereof may also form solvates such as hydrates and the invention also extends to these forms. When referred to herein it is understood that a compound of the invention or a salt thereof includes solvates.

Suitable values for $R_1$ include hydrogen, trimethylsilyl, triethylsilyl and tertiarybutyldimethylsilyl Preferably each $R_1$ is hydrogen or each $R_1$ is trimethylsilyl or triethylsilyl.

Suitable values for $R_2$ include hydroxycarbonyl, alkoxycarbonyl, aminocarbonyl, alkylthiocarbonyl, arylthiocarbonyl, heteroarylthiocarbonyl, alkanoyl, aroyl and hydroxymethyl in which the hydroxyl function is optionally substituted by $C_{1-4}$ alkyl or $C_{2-5}$ alkanoyl. Preferably $R_2$ is hydroxycarbonyl, alkoxycarbonyl for example methoxycarbonyl, hydroxymethyl, alkanoyl for example acetyl, aroyl for example benzoyl, or heteroarylthiocarbonyl for example 2-pyridylthiocarbonyl.

Where one of X and Y is hydrogen, suitable values for the other include hydroxy; $C_{1-4}$ alkoxy or $C_{3-8}$ cycloalkoxy optionally substituted by carboxy, alkoxycarbonyl, hydroxy, alkyl, alkoxy, halogen, or amino optionally substituted by $C_{1-6}$ alkyl; phenoxy and benzyloxy in each of which the benzene ring is optionally substituted by carboxy, alkoxycarbonyl, hydroxy, alkyl, alkoxy, halogen, or amino optionally substituted by $C_{1-6}$ alkyl, and the sugar residue:

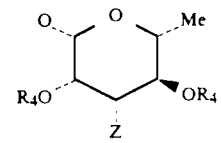

in which each $R_4$ is independently hydrogen or a silyl protecting group, and Z is an amino group, a derivatised amino group or a protected amino group.

Favourably $R_4$ is hydrogen, trimethysilyl or triethylsilyl and Z is an amino group or a protected amino group, $-NHR_3$.

Values for $R_3$ include hydrogen, acetyl, trifluoroacetyl, 9-fluorenylmethoxycarbonyl, trichloroethoxycarbonyl, 2-methylsulphonylethoxycarbonyl and 2-trimethylsilylethoxycarbonyl. Preferably $R_3$ is hydrogen, acetyl, trifluoroacetyl or 9-fluorenylmethoxycarbonyl.

There is a sub-group of compounds within formula (I) of formula (II), or a salt thereof:

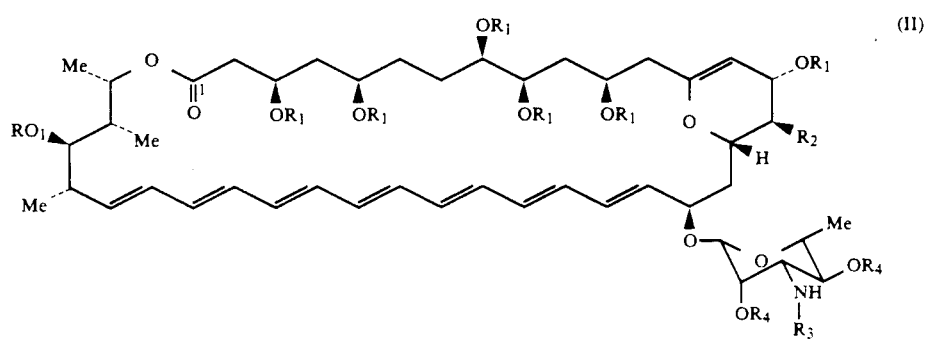

wherein $R_1$ and $R_2$ are as defined in formula (I), $R_3$ is hydrogen or an amine protection group and each $R_4$ is independently hydrogen or a silyl protecting group.

There is a second sub-group of compounds within formula (I) of formula (III):

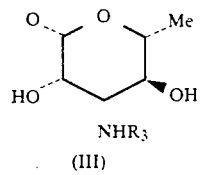

(III)

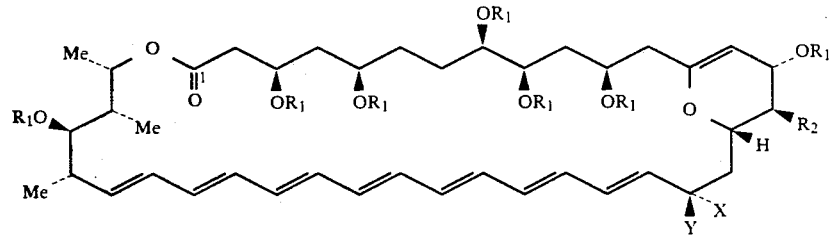

wherein $R_1$ and $R_2$ are as defined in formula (I), and X and Y together with the carbon atom to which they are bonded are a carbonyl group.

A further sub-group of compounds within formula (I) is of formula (IV), or a salt thereof:

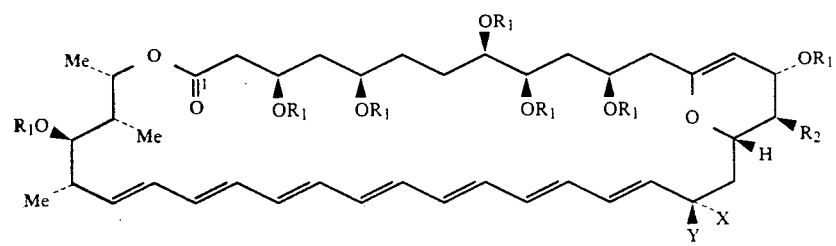

wherein $R_1$ and $R_2$ are as defined in formula (I), one of X and Y is hydrogen and the other is selected from hydroxy; $C_{1-4}$ alkoxy or $C_{3-8}$cycloalkoxy optionally substituted by carboxy, alkoxycarbonyl, hydroxy, alkyl, alkoxy, halogen, or amino optionally substituted by $C_{1-6}$ alkyl; phenoxy and benzyloxy in each of which the benzene ring is optionally substituted by carboxy, alkoxycarbonyl, hydroxy, alkyl, alkoxy, halogen or amino optionally substituted by $C_{1-6}$ alkyl.

There is a preferred sub-group of compounds within formula (I) of formula (V), or a pharmaceutically acceptable salt thereof:

wherein $R_3$ is hydrogen or an amine protection group; or X and Y together with the carbon atom to which they are bonded are a carbonyl group.

Suitable values for $R_2$ in compounds of formula (V) include hydroxycarbonyl, alkoxycarbonyl, aminocarbonyl, alkylthiocarbonyl, arylthiocarbonyl, heteroarylthiocarbonyl, alkanoyl, aroyl, and hydroxymethyl in which the hydroxy function is optionally substituted by $C_{1-4}$ alkyl or $C_{2-5}$ alkanoyl. Preferably $R_2$ is hydroxycarbonyl, alkoxycarbonyl for example methoxycarbonyl, hydroxymethyl, acetyl or benzoyl.

Where one of X and Y in compounds of formula (V) is hydrogen, values for the other include hydroxy; $C_{1-4}$ alkoxy or $C_{5-6}$ cycloalkyoxy optionally substituted by

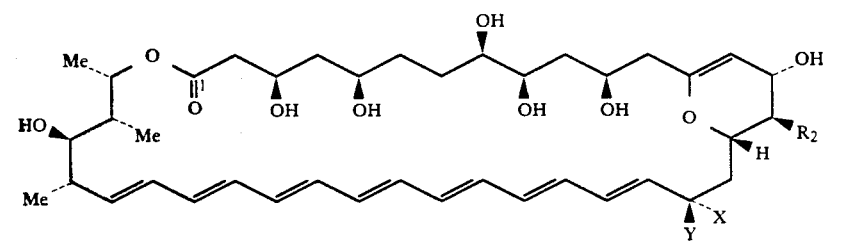

(V)

wherein $R_2$ is as defined in formula (I); one of X and Y is hydrogen and the other is selected from hydroxy; $C_{1-4}$ alkoxy or $C_{3-8}$ cycloalkoxy optionally substituted by carboxy, alkoxycarbonyl, hydroxy, alkyl, alkoxy, halogen, or amino optionally substituted by $C_{1-6}$ alkyl; phenoxy and benzyloxy in each of which the benzene ring is optionally substituted by carboxy, alkoxycarbonyl, hydroxy, alkyl, alkoxy, halogen, or amino optionally substituted by $C_{1-6}$ alkyl; or the sugar residue:

carboxy, alkoxycarbonyl, hydroxy, $C_{1-4}$ alkyl, $C_{1-4}$ alkoxy, halogen, or amino optionally substituted by $C_{1-4}$ alkyl; phenoxy and benzyloxy in each of which the benzene ring is optionally substituted by carboxy, alkoxycarbonyl, hydroxy, $C_{1-4}$ alkyl, $C_{1-4}$ alkoxy, halogen or amino optionally substituted by $C_{1-4}$ alkyl; and preferably the sugar residue:

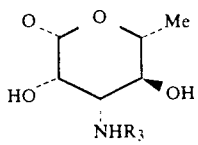

wherein $R_3$ is hydrogen or an amine protection group, more preferably $R_3$ is hydrogen.

Compounds of formula (V) have been found to have anti-fungal activity and are therefore potentially useful as pharmaceutical agents in the treatment of fungal infections in animals, including humans.

Salts, including pharmaceutically acceptable salts of compounds of the invention, may be formed conventionally, for example by reaction with the appropriate acid or base.

The compounds of formula (V) wherein $R_3$ is hydrogen or alkyl can form acid addition salts with acids, such as conventional pharmaceutically acceptable acids, for example hydrochloric, hydrobromic, phosphoric, acetic, fumaric, salicylic, citric, lactic, mandelic, tartaric, oxalic and methanesulphonic.

The compounds of formula (V) wherein $R_2$ is carboxyl can form basic addition salts with bases, such as conventional pharmaceutically acceptable bases, for example sodium hydrogen carbonate, potassium carbonate, lithium hydroxide, triethylamine, pyridine and lutidine.

The present invention also provides a process for the preparation of compounds of formula (I) which process comprises the reaction of a compound of formula (VI):

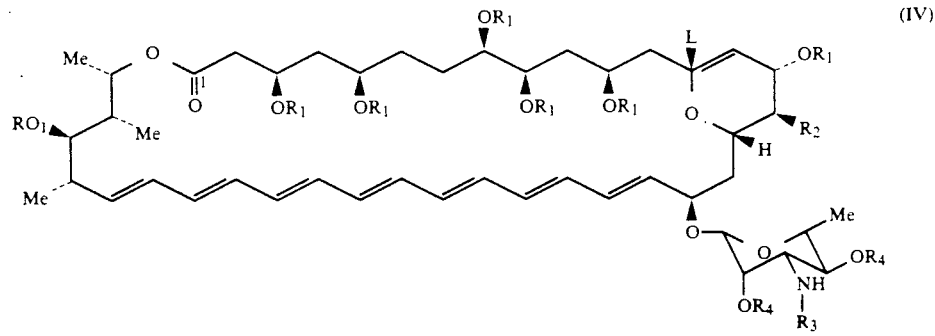

wherein L is a leaving group or a group convertible thereto, $R_1$ and $R_2$, are as defined in formula (I), $R_3$ is hydrogen or an amine protection group and each $R_4$ is independently hydrogen or a silyl protecting group, with a silylating agent, to give a compound of formula (II), and thereafter, as required:

a) converting $R_1$ to further values of $R_1$, $R_2$ to further values of $R_2$, $R_3$ to further values of $R_3$ and $R_4$ to further values of $R_4$;
b) optionally cleaving the sugar moiety to give a compound of formula (III);
c) optionally reducing the 19-position carbonyl group of a compound of formula (III) to give a compound of formula (IV) in which one of X and Y is hydrogen and the other is hydroxy; and
d) optionally derivatising the 19-hydroxyl function so formed to give further compounds of formula (IV).

Suitable values for L include hydroxy, alkoxy, for example methoxy, acyloxy, and thiol derivatives.

Suitable silylating agents include inter alia trimethylsilyl trifluoromethanesulphonate and triethylsilyl trifluoromethanesulphonate.

The preparation of compounds of formula (II) from compounds of formula (VI) in which the leaving group L is a derivatised hydroxy group, is readily effected under standard silylating conditions.

The reaction of compounds of formula (VI) with silylating agents may be carried out in an inert solvent, for example dichloromethane, under an inert atmosphere at reduced temperatures, for example 0°–5° C. The reaction is conveniently effected using an excess of the silylating agent in the presence of a weak base, for example a pyridine derivative such as 2,6-lutidine. Alternatively, a liquid base may replace the solvent. The reaction time is dependent of the size of the silyl group, ranging from less than one minute for a trimethylsilyl group to several hours for larger silyl groups.

Where any $R_1$ in compounds of formula (VI) is hydrogen, and an excess of silylating agent is used, the free hydroxyl groups are silylated to give a compound of formula (II) in which each $R_1$ is a silyl protecting group.

Use of less than one equivalent of silylating agent per free hydroxyl group ($R_1$, $R_4$=H) will result in partial silylation of the free hydroxyl groups.

$R_1$ and $R_4$ silyl protecting groups may be removed to generate compounds of formula (II) in which $R_1$ and $R_4$ are hydrogen using known deprotection methods, for example a solution of hydrogen fluoride—pyridine in tetrahydrofuran at elevated, normal or reduced temperatures.

Further transformations of compounds of formula (II) to give compounds of formulae (III) and (IV) are conveniently carried out using compounds of formulae (II) and (III) respectively in which $R_1$ (and $R_4$ where present) are silyl protecting groups. Compounds of formulae (III) and (IV) in which $R_1$ is a silyl protecting group may be converted to compounds of formulae (III) and (IV) in which $R_1$ is hydrogen using hydrogen fluoride—pyridine as described above.

Compounds of formulae (II), (III) and (IV) in which $R_1$ (and $R_4$ where present) are hydrogen are compounds of formula (V). Compounds of formula (V) may thus be prepared from compounds of formulae (II), (III) and (IV) in which any $R_1$ or ($R_4$ where present) is a silyl protecting group using hydrogen fluoride-pyridine.

Conversion of $R_2$ in compounds of formula (I) to further values of $R_2$ may be carried out using functional group interconversion procedures generally used in the field of polyene macrolide chemistry. For example, an $R_2$ carboxylic acid may be esterified to give an $R_2$ methyl ester using diazomethane in an ether solvent at reduced temperatures. An $R_2$ methyl ester may be reduced to $R_2$ hydroxymethyl using sodium borohydride in an alcoholic solvent, for example methanol.

An $R_2$ carboxylic acid group may be converted to an activated form suitable for transformation to a lower oxidation state such as an $R_2$ ketone or aldehyde. For example, an $R_2$ carboxylic acid may be converted to an $R_2$ heteroarylthioester, such as 2-pyridylthiocarbonyl, which may undergo reaction with an organometallic reagent to give an $R_2$ ketone, or alternatively may be reduced to $R_2$ hydroxymethyl and re-oxidised to $R_2$ aldehyde.

An $R_2$ carboxylic acid group may be converted to $R_2$ 2-pyridylthiocarbonyl using 2-thiopyridyl chloroformate in an inert solvent such as tetrahydrofuran, diethyl ether or dichloromethane, preferably diethyl ether, at temperatures ranging from reduced to elevated, such as from $-20°$ C. to $50°$ C., preferably $0°$ C. to room temperature.

Organometallic reagents suitable for reaction with an $R_2$ activated carboxylic acid derivative include reagents in which the metallic element of the metallic residue may be magnesium, lithium, copper, zinc, manganese or cadmium.

Preferably the organometallic reagent is an organomagnesium halide or Grignard Reagent such as an organomagnesium bromide or iodide, for example methylmagnesium bromide or phenylmagnesium bromide.

The reaction with the organometallic reagent may be carried out under conditions generally used for such reactions, for example using anhydrous reagents under an inert atmosphere and at reduced temperature.

The reaction is preferably conducted using an excess of a Grignard Reagent, for example from 2 to 30 molar equivalents and preferably from 5 to 15 molar equivalents, in an inert solvent such as tetrahydrofuran or diethylether. The reaction is generally carried out at reduced temperature in the range $-78°$ C. to room temperature and preferably in the range $-20°$ C. to room temperature. Reaction times may vary between 0.1 and 6 hours but a reaction time between 0.1 and 1 hour is generally sufficient.

A suitable reducing agent for reaction with an $R_2$ carboxylic acid derivative is lithium borohydride. The reaction may be carried out in an inert solvent such as diethyl ether or tetrahydrofuran, preferably diethyl ether.

The oxidation of the resulting $R_2$—$CH_2OH$ group may be carried out using modified Swern oxidising conditions such as a mixture of trifluoroacetic anhydride, dimethyl sulphoxide, triethylamine and 1,1,3,3-tetramethylurea in dichloromethane.

It may be convenient or necessary to carry out these functional group interconversions using compounds of formula (I) in which $R_1$ and $R_4$ (where present) are silyl protecting groups and $R_3$ (where present) is an amine protection group.

Suitable $R_3$ amine protection groups for conversion of an $R_2$ carboxylic acid to an $R_2$ ketone include acetyl and trifluoroacetyl, preferably trifluoroacetyl.

Suitable $R_3$ amine protection groups for reduction of an $R_2$ carboxylic acid or ester include acetyl and 9-fluorenylmethoxycarbonyl, preferably 9-fluorenylmethoxycarbonyl.

$R_3$ amine protection groups in compounds of formula (II) may be introduced or removed, as required, by standard procedures. For example, an $R_3$ acetyl or trifluoroacetyl amine protection group may be introduced by reaction of the primary amine ($R_3=H$) with acetic anhydride or ethyl trifluoroacetate in a methanol-dimethyl sulphoxide or methanol-dimethylformamide solvent mixture at reduced to normal temperatures, for example at $0°$ C.

An $R_3$ 9-fluorenylmethoxycarbonyl group may be introduced by addition of N-(9-fluorenylmethoxy carbonyloxy)succinimide to a slurry of the primary amine ($R_3=H$) in methanol-dimethylformamide under anhydrous conditions in the presence of a base such as pyridine.

Alternatively, an $R_3$ 9-fluorenylmethoxycarbonyl amine protection group may be introduced by addition of 9-fluorenylmethyl chloroformate to a solution of the primary amine ($R_3=H$) in methanol-dimethylformamide under anhydrous conditions, in the presence of a base such as potassium carbonate.

Where $R_3$ in compounds of formula (II) is hydrogen, conversion of a readily removable $R_3$ amine protection group to $R_3$ hydrogen may be carried out under basic conditions.

An $R_3$ amine protection group such as trifluoroacetyl may be removed using a base such as ammonia or potassium carbonate in anhydrous methanol.

An $R_3$ amine protection group, such as 9-fluorenylmethoxycarbonyl, may be removed under basic conditions in a solvent such as methanolic dimethyl sulphoxide. Suitable bases for amine deprotection include ammonia, dialkylamines such as dimethylamine and diethylamine, trialkylamines such as triethylamine, cyclic amines and especially cyclic secondary amines such as morpholine, piperazine and more especially piperidine, and diazabicyclic amine bases such as 1,5-diazabicyclo[4.3.0]non-5-ene (DBN) and preferably 1,8-diazabicyclo[5.4.0]undec-7-ene (DBU).

The amine deprotection may be carried out using from 1-10 equivalents of base, preferably from 1-2 equivalents, at reduced or elevated temperatures, for example from $-30°$ C. to $50°$ C. and preferably from $0°$ C. to room temperature, over a time period ranging from 1 minute to 5 hours and preferably from 30 minutes to 2.5 hours.

Deglycosidation of compounds of formula (II) to give compounds of formula (III) may be carried out by literature procedures. Nicolaou et al. [J. Chem. Soc. Chem. Commun., 686, (1987)] describe the use of N-bromosuccinimide in carbon tetrachloride and S. Masamune et al. [Tetrahedron Letters, 29, 447, (1988)] describe the use of dichlorodicyanobenzoquinone (DDQ) in tetrahydrofuran.

The 19-position carbonyl group of the aglycone derivatives of formula (III) may be reduced to give compounds of formula (IV) using standard reduction procedures, for example using sodium borohydride in an alcoholic solvent such as methanol, at room temperature. Where $R_2$ in the compound of formula (III) is a carboxylic ester, for example a methyl ester, the 19-position carbonyl group may be selectively reduced, or alternatively concomitant reduction of the ester function may be effected to give $R_2$ hydroxymethyl, using excess reducing agent.

The 19-hydroxyl group of compounds of formula (IV) may be derivatised to give compounds of formula (I) in which X is hydrogen and Y is other than hydroxy using standard alkylation or acylation procedures.

The intermediate compound of formula (VI) in which L is hydroxy, $R_1$ is hydrogen, $R_2$ is a carboxylic acid group, $R_3$ is hydrogen and $R_4$ is hydrogen is the natural product, amphotericin B and is commercially available.

Further intermediate compounds of formula (VI) in which L is hydroxy and $R_1$ and $R_4$ are hydrogen may be prepared from the natural product using the procedures described above for interconversion of variables $R_2$ and $R_3$. Compounds of formula (VI) in which $R_1$ and $R_4$ are hydrogen and L is other than hydroxy may be prepared by selective derivatisation of the anomeric 13-position hydroxyl group of amphotericin B, or derivatives thereof in which $R_2$ is a carboxylic acid or derivative thereof and/or $R_3$ is hydrogen or an amine protection group. For example, compounds of formula (VI) in which L is alkoxy may be prepared by reaction of compounds of formula (VI) in which L is hydroxy with the appropriate alcohol in the presence of an acid catalyst, for example camphor sulphonic acid, under anhydrous conditions.

Compounds of formula (VI) in which $R_1$ and $R_4$ are silyl protecting groups may be prepared by selective silylation of amphotericin B and derivatives thereof. Silylation reactions may be carried out using standard procedures as hereinbefore described but elimination of the anomeric 13-position substituent may be precluded by suitable choice of silylating reagent and solvent, for example using hexane or diethylether as solvent.

Compounds of formula (I) and salts thereof are useful as intermediates in the preparation of purified amphotericin B and derivatives thereof, in particular anti-fungally active derivatives of amphotericin B.

The compounds of the formula (V) and their pharmaceutically acceptable salts are anti-fungal agents, potentially useful in combating fungal infections in animals, including humans. For example they are potentially useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They may also be used in the treatment of systemic fungal infections caused by, for example *Candida albicans, Cryptococcus neoformans, Aspergillus fumigatus,* Coccidioides, Paracoccidioides, Histoplasma or Blastomyces spp. They may also be use in treating eumycotic mycetoma, chromoblastomycosis, and phycomycosis.

The invention further provides a pharmaceutical composition comprising a compound of the formula (Va) or a pharmaceutically acceptable salt thereof:

bonyl, hydroxy, alkyl, alkoxy, halogen, or amino optionally substituted by $C_{1-6}$ alkyl; or the sugar residue:

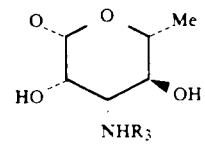

wherein $R_3$ is hydrogen or an amine protection group; or X and Y together with the carbon atom to which they are bonded are a carbonyl group, together with a pharmaceutically acceptable diluent or carrier. The composition is preferably for human use in tablet, capsule, injectable or cream form.

For human use, the antifungal compounds of the formula (Va) (or pharmaceutically acceptable salts thereof) can be administered alone, but will generally be administered in admixture with a pharmaceutical carrier selected with regard to the intended route of administration and standard pharmaceutical practice. For example, they may be administered orally in the form of a tablet containing such excipients as starch or lactose, or in a capsule or ovule either alone or in admixture with excipients, or in the form of an elixir or suspension containing a flavouring or colouring agent. They may be injected parenterally, for example, intravenously, intramuscularly or subcutaneously. For parenteral administration, they are best used in the form of a sterile aqueous solution which may contain other substances, for example, enough salts or glucose to make the solution isotonic.

For oral and parenteral administration to human patients, it is expected that the daily dosage level of the antifungal compounds of the formula (Va) will be from 0.1 to 1 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

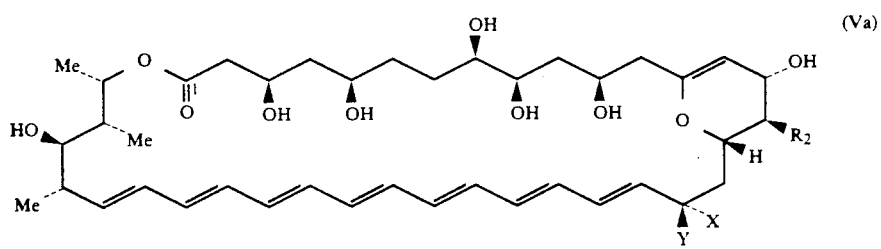

wherein $R_2$ is as defined in formula (I); one of X and Y is hydrogen and the other is selected from hydroxy; $C_{1-4}$ alkoxy or $C_{3-8}$ cycloalkoxy optionally substituted by carboxy, alkoxycarbonyl, hydroxy, alkyl, alkoxy, halogen, or amino optionally substituted by $C_{1-6}$ alkyl; phenoxy and benzyloxy in each of which the benzene ring is optionally substituted by carboxy, alkoxycar- Alternatively, the antifungal compounds of formula (Va) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

Within the indicated dose range, no adverse toxicological effects have been observed with the compounds of the invention which would preclude their administration to suitable patients for the treatment of fungal infections.

The present invention further provides a compound of formula (Va) or a pharmaceutically acceptable salt thereof for use as a therapeutic substance, particularly for use in the treatment of fungal infections.

The present invention additionally provides a method of treatment of fungal infections in animals, including humans, which comprises administering an effective anti-fungal amount of a compound of formula (Va) or a pharmaceutically acceptable salt thereof to the animal.

The present invention also provides the use of a compound of formula (Va) or a pharmaceutically acceptable salt thereof for the manufacture of a medicament for use as an active therapeutic substance, particularly in the treatment of fungal infections in animals, including humans.

The following Descriptions illustrate the preparation of novel intermediates to the invention. The following Examples 1 to 22 illustrate the preparation of compounds of the invention, and Example 23 illustrates the utility of compounds of the invention in the preparation of purified amphotericin B.

Description 1

N-Acetyl-13-O-methyl-amphotericin B (D1)

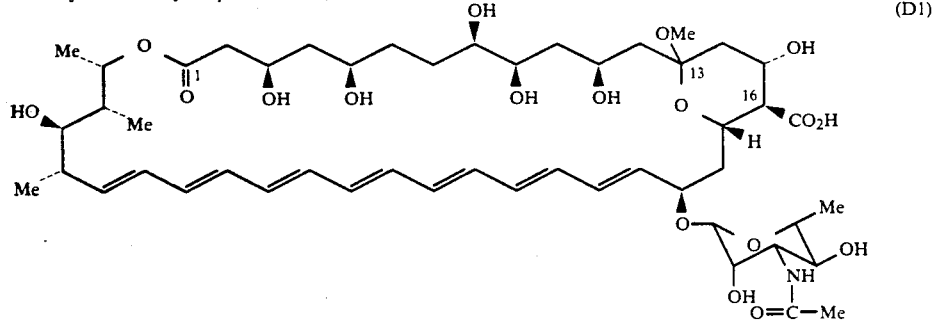

N-Acetyl amphotericin B[1](697 mg, 0.71 mmol) and anhydrous d-10-camphorsulphonic acid (57.5 mg, 0.25 mmol) were stirred in a mixture of dry methanol (15 ml) and dry tetrahydrofuran (2.5 ml) at room temperature under nitrogen for 0.5 hours. Triethylamine (26 mg, 0.036 ml, 0.26 mmol) was added, the mixture was concentrated to approximately 3 ml and added to diethylether (400 ml). The precipitate was filtered and washed with ethyl acetate to give the title compound as a yellow powder.

[1]Nicolaou et al., J. American Chem. Soc., 110, 4660, (1988).

Hplc: Reverse phase ODS 5μ 250×4.6 mm column; eluent 78% Methanol-22% pH 3 phosphate buffer—1 ml/min; detection wavelength 360 nm; Retention time: 4.8 minutes.

Description 2

N-(9-Fluorenylmethoxycarbonyl)amphotericin B (D2)

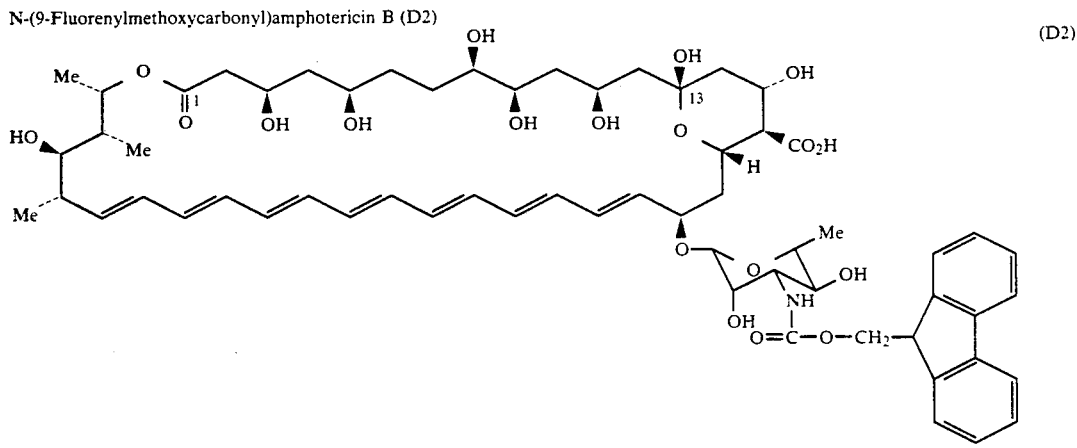

Method A

To a solution of amphotericin B (5.0 g, 5.4 mmol) in dry dimethylsulphoxide (50 ml) and dry methanol (15 ml) was added dry pyridine(0.53 ml, 6.5 mmol). Under a nitrogen atmosphere was added solid N-(9-fluorenylmethoxycarbonyloxy)succinimide (2.59 g, 7.6 mmol). After stirring for 1 hr a further portion of N-(9-fluorenylmethoxycarbonyloxy)succinimide (0.28 g 0.8 mmol) was added. After a further 0.25 hrs glacial acetic acid (0.5 ml, 8.7 mmol) was added, the solution was diluted with methanol (35 ml) and poured into diethyl ether (5L). The precipitate was filtered, washed with diethyl ether and dried to give the title compound (D2) which was used without further purification.

Method B

To a solution of amphotericin B (0.50 g, 0.54 mmol) and anhydrous potassium carbonate (0.17 g, 1.2 mmol)

in dry dimethylsulphoxide (10 ml) and dry methanol (2 ml) under a nitrogen atmosphere at 0° C., was added solid 9-fluorenylmethyl chloroformate (0.21 g, 0.81 mmol). After stirring for 1 hour a further portion of 9-fluorenylmethyl chloroformate (0.04 g, 0.17 mmol) was added. After 0.25 hours the reaction mixture was poured into distilled water (200 ml). The precipitate was collected by centrifugation, dissolved in methanol and evaporated in vacuo. The residue was dissolved in the minimum volume of a mixture of tetrahydrofuran and methanol (1:1) and poured into distilled water (200 ml, adjusted to pH 3.2 by the addition of glacial acetic acid). The preciptate was centrifuged, washed with water and dried in vacuo to give the title compound (D2) which was used without further purification.

by centrifugation, washed with diethyl ether, dissolved in methanol and evaporated in vacuo.

The crude material was purified by means of medium pressure column chromatography on silica-gel eluting with ethyl acetate/methanol mixtures. The title compound (D3) was obtained as a yellow solid.

$\delta H_{270}MHz[d_8THF/d_4\text{-}MeOH]$ 7.78 (2H,d,J 6.9Hz), 7.70 (2H,d,J 7.4Hz), 7.35 (2H,dd,J 7.4 and 6.3Hz), 7.28 (2H,t, 7.4Hz), 6.63–5.93 (13H, complex), 5.50 (1H,m), 5.32 (1H,dd,J 10.2 and 14.8Hz), 4.75–4.04 (10H, complex), 3.90–3.00 (8H, complex), 3.74 (3H,s), 2.50–1.15 (19H, complex), 1.28 (3H,d,J 6.2Hz), 1.20 (3H,d,J 6.3Hz), 1.10 (3H,d,J 6.3Hz) and 0.99 (3H,d,J 7.2Hz)ppm.

Description 4

N-(9-Fluorenylmethoxycarbonyl)-13-O-methyl-amphotericin B (D4)

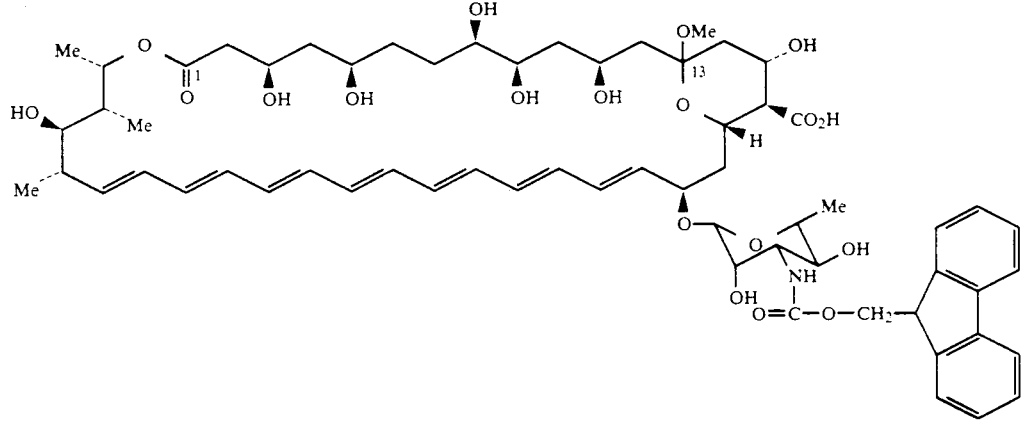

Description 3

N-(9-Fluorenylmethoxycarbonyl)amphotericin B methyl ester (D3)

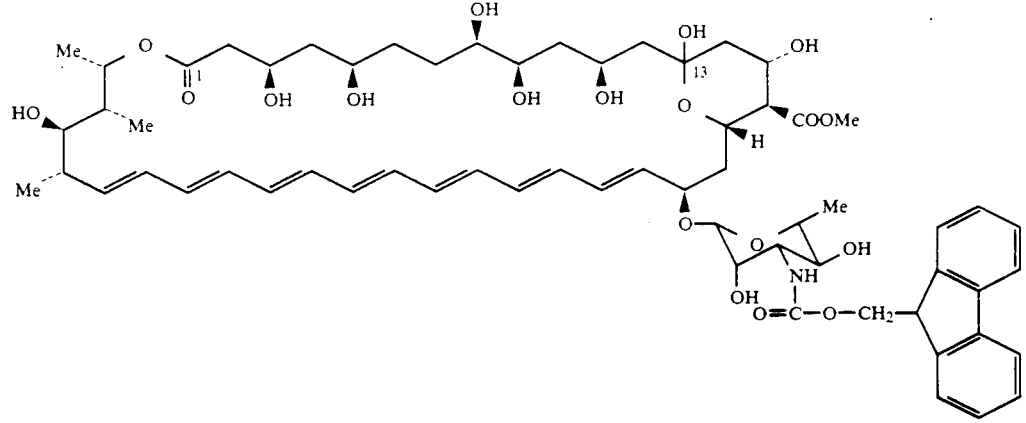

N-(9-Fluorenylmethoxycarbonyl)amphotericin B

Crude N-(9-fluorenylmethoxycarbonyl)amphotericin B (D2) (0.36 g, 0.31 mmol) was dissolved in 1:1 dimethylsulphoxide and methanol (20 ml). At 0° C. and with stirring, a solution of diazomethane in diethyl ether (25 ml) was added over 0.3 hours. The diazomethane was generated from Diazald® (0.39 g, 1.8 mmol); potassium hydroxide (0.18 g, 3.2 mmol); water (1 ml) and 2-(2-ethoxyethoxy)ethanol (2 ml). The reaction was stirred for a further 1.5 hours and then quenched cautiously with glacial acetic acid. The product was precipitated by pouring into diethyl ether. It was collected (D2) (1.85 g, 1.61 mmol) and d-10-camphorsulphonic acid (156 mg, 0.67 mmol) were stirred in dry tetrahydrofuran (10 ml)/methanol (60 ml) at room temperature under nitrogen. After 15 minutes, triethylamine (0.14 ml, 102 mg, 1.01 mmol) was added, the mixture was filtered, concentrated to ca. 10 ml and poured into diethylether/n-hexane (800 ml 1:1). The precipitated product was collected by centrifugation, washed with diethylether/ethylacetate (1:1) and dried to give the title compound (D4) as a yellow powder.

HPLC: Reverse phase ODS 5 μ 250×4.6 mm column; eluent 80% methanol-20% pH 3 phosphate buffer—1 ml.min⁻¹; detection wavelength 350 nm; retention time: 7.6 minutes.

Description 5

N-Trifluoroacetylamphotericin B (D5)

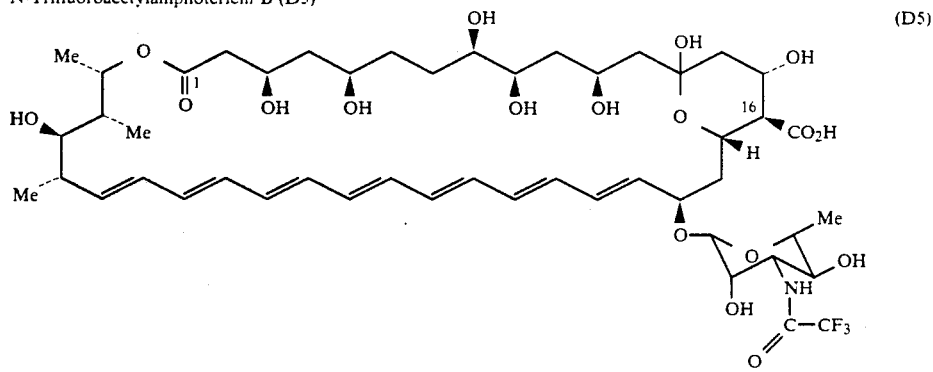

A mixture of amphotericin B (2.20 g, 2.38 mmol), ethyl trifluoroacetate (0.51 g, 0.43 ml, 3.57 mmol)) and diisopropylethylamine (0.46 g, 0.62 ml, 3.57 mmol) in dry dimethylformamide (100 ml)/methanol (10 ml) was stirred at room temperature under nitrogen. After stirring overnight, the mixture was poured into diethylether (4L) containing glacial acetic acid (ca. 1 ml). The precipitated solid was collected by filtration, washed with diethyl ether and ethyl acetate, and dried to give the title compound (D5) as a brown powder. HPLC: Reverse phase ODS 5μ 250×4.6 mm column; eluent 78% methanol-22% pH 3 phosphate buffer—1 ml.min⁻¹; detection wavelength 350 nm; retention time 7.9 minutes. δH 270 MHz(d₄-methanol/d₅-pyridine 1:1) 6.75–6.23(13H series of m), 5.75–5.40(2H, m, partially masked by solvent peaks), 5.0–4.60(5H, series of m), 4.49(1H, m), 4.37(1H, dd, J 3.0, 10.5Hz), 4.27(1H, d, J 3.0Hz), 4.05–3.80(3H, m), 3.57(1H, m), 3.45–3.30(2H, m), 2.70–2.30(6H, series of m), 2.28–1.30(13H, series of m), 1.43(3H, d, J 6.3Hz), 1.36(3H, d, J 6.6Hz), 1.25(3H, d, J 6.3Hz), 1.18(3H, d, J 7.2Hz),ppm. IR ν$_{max}$ (KBr disc): 3400 (broad), 2920, 1720, 1552, 1379, 1323, 1172, 1063, 1010, 883, 847, 795 cm⁻¹.

· Example 1

N-Acetyl-3,5,8,9,11,15,35,2′,4′-nona-O-trimethylsilyl-13,14-anhydroamphotericin B methyl ester (E1)

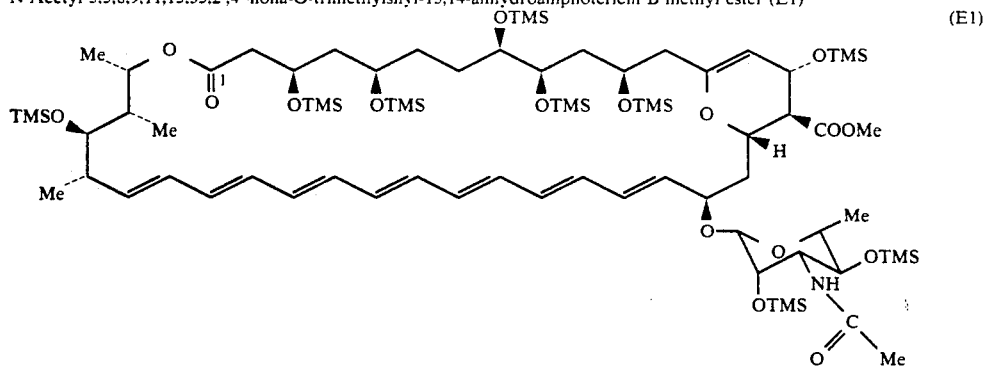

N-Acetylamphotericin B methyl ester1 (0.3 g, 0.306 mmol), suspended in dry dichloromethane (10 ml) at 0° under a nitrogen atmosphere, was treated with 2,6-lutidine (0.605 ml, 5.19 mmol) and then, dropwise, with trimethylsilyl trifluoromethanesulphonate (0.77 ml, 3.98 mmol). The solution was allowed to stir for 0.5 hours and was then evaporated in vacuo.

The crude material was purified by means of medium pressure column chromatography on silica-gel eluting with n-hexane and n-hexane/ethyl acetate mixtures.

The title compound (E1) was obtained as an orange gum which was stored under high vacuum to remove any residual 2,6-lutidine.

λmax(CHCl₃) 410 nm; νmax(CHCl₃) 2950,1725,1670,1370, 1245,1160,1100,1070,1000 and 840 cm⁻¹; δH(400MHz) [(CD₃)2CO]6.72 (1H,d, J 9.3 Hz), 6.49–6.11 (12H, complex), 5.89 (1H,dd, J 6.0 and 15.1 Hz), 5.61 (1H,dd, J 9.2 and 14.8 Hz), 4.90 (1H,m), 4.68 (1H,dd, J 1.5 and 8.8 Hz), 4.62 (1H,m), 4.55 (1H,d, J 1.0 Hz), 4.50 (1H,d, J 1.7 Hz), 4.18 (2H,m), 3.98 (2H,m), 3.88 (3H,m), 3.71 (3H,s), 3.66 (2H,m), 3.46 (1H,dd, J 9.7 and 9.0 Hz), 3.31 (1H,dq, J 6.1 and 9.0 Hz), 2.56 (1H,dd, J 8.8 and 10.9 Hz), 2.47 (2H,d, J 6.3 Hz), 2.42 (1H,bq, J 6.8 and 8.9 Hz), 2.12 (2H,m), 2.0 (1H,m), 2.00–1.84 (7H,m,including s), 1.75–1.59 (3H, complex), 1.58–1.40 (3H,complex), 1.19 (3H,d, J 6.1 Hz), 1.16 (3H,d, J 6.2 Hz), 1.03 (3H,d, J 6.7 Hz), 0.96 (3H,d, J 7.1 Hz), 0.159 (9H,s), 0.157 (9H,s), 0.154 (9H,s), 0.142 (9H,s), 0.136 (9H,s), 0.132 (9H,s), 0.118 (9H,s), 0.089 (9H,s) and 0.070 (9H,s) ppm.

Mass Spectrum: FAB (3-NOBA Matrix) Isotope Cluster Abundance Calculations. Mass 1612, %′ intensity 100, mass 1613, % intensity 91.6. Hplc: Normal phase using Waters Z-module radially compressed silica column. Eluent: 18% ethyl acetate in n-hexane. Flow rate: 3 ml/min., detection at 406 nm. Retention time: 6.2 minutes.

¹Nicolaou et al., J. American Chem. Soc., 110, 4660, (1988).

EXAMPLE 2

3,5,8,9,11,15,35-Hepta-O-trimethylsilyl-13,14-anhydro-19-dehydro-19-keto-amphoteronolide B methyl ester (E2)

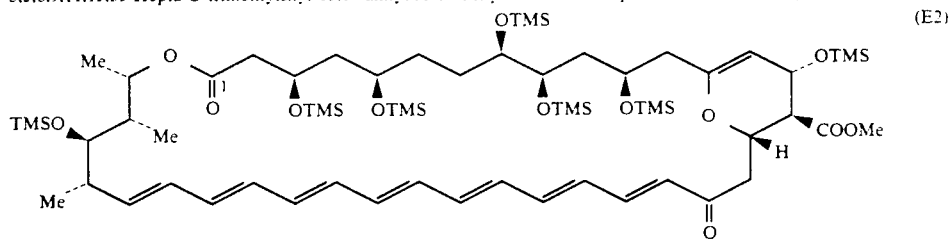

N-Acetyl-3,5,8,9,11,15,35,2',4'-nona-O-trimethylsilyl-13,14-anhydroamphotericin B methyl ester (E1) (0.14 g, 0.087 mmol) in dry tetrahydrofuran (2 ml) was treated with a solution of 2,3-dichloro-5,6-dicyano-1,4-benzoquinone (20 mg, 0.088 mmol) in dry tetrahydrofuran (2 ml). The mixture was stirred for 1.75 hours then evaporated in vacuo. The crude product was purified using medium pressure column chromatography on silica gel eluting with n-hexane and n-hexane/ethyl acetate mixtures. The title compound (E2) was obtained as an orange gum and has; λmax (CHCl$_3$) 430 nm; νmax (CH$_2$Cl$_2$) 2950,1730(sh), 1725,1710(sh),1630,1590,1540,1350,1300,1240,1160,1150, 1070,1010,870,840 cm$^{-1}$; δH (400MHz) [(CD$_3$)2CO]7.55 (1H,dd, J 15.6 and 11.0 Hz), 7.11 (1H,dd, J 14.6 and 11.1 Hz), 6.74 (1H,dd, J 14.6 and 10.5 Hz), 6.55 (2H,2xdd, J 14.5 and 11.0 and J 14.5 and 11.3 Hz), 6.43 (1H,dd, J 14.7 and 11.1 Hz), 6.40 (1H,dd, J 14.8 and 11.1 Hz), 6.34 (1H,dd, J 14.6 and 11.0 Hz), 6.29 (1H,dd, J 14.6 and 11.3 Hz), 6.28–6.15 (3H,m), 6.10 (1H,d, J 15.8 Hz), 5.55 (1H,dd, J 14.7 and 9.6 Hz), 4.68 (1H,dd, J 8.4 and 1.8 Hz), 4.63 (1H,m), 4.57 (1H,d, J 1.9 Hz), 4.08 (1H,m, J 10.2 and 1.2 Hz), 4.07 (1H,m), 4.02 (1H,m), 3.88 (1H,m), 3.75 (1H,dd, J 8.8 and 2.8 Hz), 3.71 (3H,s), 3.70 (1H,m), 3.60 (1H,dd, J 10.2 and 4.6 Hz),3.21 (1H,dd, J 12.8 and 10.1 Hz), 2.58 (1H,dd, J 10.4 and 8.5 Hz), 2.52 (1H,d, J 2.0 Hz), 2.50 (1H,d, J 3.9 Hz), 2.40 (1H,m), 2.31 (1H,d, J 11.9 Hz), 2.20 (1H,dd, J 12.9 and 1.6 Hz), 2.06 (1H,m), 1.90–1.78 (3H,m), 1.72–1.52 (6H,m), 1.39 (1H,m), 1.12 (3H,d, J 6.1 Hz), 0.98 (3H,d, J 6.7 Hz), 0.93 (3H,d, J 7.0 Hz) and 0.20–0.05 (63H,7xs) ppm.

Mass Spectrum FAB (3-NOBA sodium matrix) observed mass 1299,1300—calculated mass for C$_{63}$H$_{117}$O$_{13}$Si$_7$Na, 1300.

Hplc: Normal phase using Waters Z-module radially compressed silica column. Eluent: 13.3% ethyl acetate in n-hexane. Flow rate: 3 ml/min, detection at 406 nm. Retention time: 3.6 minutes.

EXAMPLE 3

3,5,8,9,11,15,35-Hepta-O-trimethylsilyl-13,14-anhydroamphoteronolide B, methyl ester (E3)

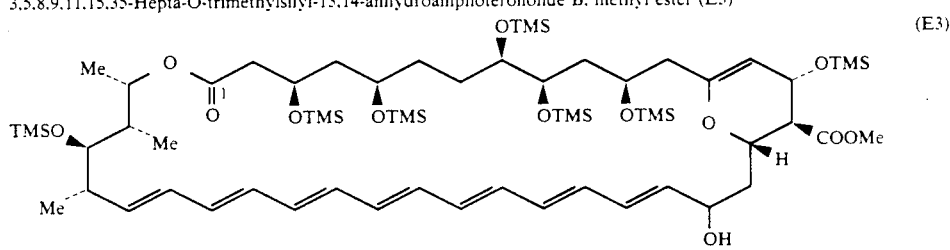

3,5,8,9,11,15,35-Hepta-O-trimethylsilyl-13,14-anhydro-19-dehydro-19-keto-amphoteronolide B, methyl ester (E2) (32 mg, 0.025 mmol), dissolved in dry methanol (2 ml) was cooled to 0° C. under nitrogen and treated with sodium borohydride (1 mg, 0.027 mmol). The mixture was stirred for 0.25 hours and then poured into a mixture of saturated ammonium chloride solution (20 ml) and diethyl ether (20 ml). The organic phase was separated, washed with brine, dried over anhydrous magnesium sulphate, filtered and evaporated to give a yellow gum.

The title compound (E3) was obtained by medium pressure column chromatography on silica gel eluting with n-hexane/ethyl acetate mixtures. δH(270MHz) [(CD$_3$)2CO] 6.65–6.25 (12H,m), 6.05 (1H,dd, J 15.0 and 6.0 Hz), 5.80 (1H,dd, J 14.5 and 9.0 Hz), 4.95 (1H,m), 4.80 (1H,d, J 8.8 Hz), 4.65 (1H,m), 4.60 (1H,d, J 1.6 Hz) 4.30 (2H,m), 4.05 (4H,m), 3.80 (3H,s), 3.25 (2H,m), 2.6 (4H,m), 2.25 (1H,m), 2.15–1.45 (13H,m), 1.25 (3H,d, J 6.0 Hz), 1.20 (3H,d, J 6.9 Hz), 1.05 (3H,d, J 7.2 Hz) and 0.25 (63H,m) ppm.

Mass Spectrum: FAB (3-NOBA/sodium matrix) observed mass 1302 calculated mass for C$_{63}$H$_{119}$O$_{13}$Si$_7$Na = 1302. Hplc: Normal phase using Waters Z-module radially compressed silica column. Eluent: 20% ethyl acetate in n-hexane. Flow rate: 3ml/min, detection at 406 nm. Retention time: 4.65 minutes.

EXAMPLE 4

N-Acetyl-3,5,8,9,11,15,35,2',4'-nona-O-triethylsilvyl-13,14-anhydroamphotericin B (E4)

-continued

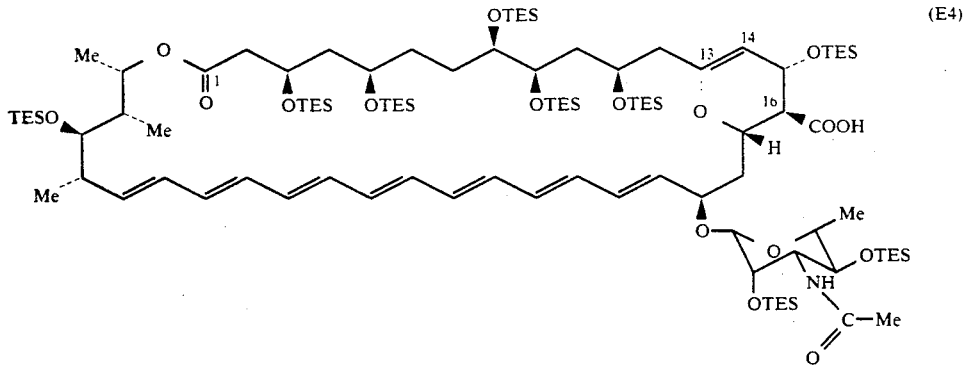
(E4)

Method A

The compound of Description 1 (600 mg) was suspended in dry dichloromethane (25 ml) at 0° C. and 2,6-lutidine (1.85 g,2.01 ml,0.017 mol) followed by triethylsilyl trifluoromethanesulphonate (2.11 g,1.80 ml,0.008 mol) were added dropwise via syringe. After stirring at 0° C. for 1 hour the solvent was evaporated and the residue was dissolved in n-hexane, filtered and the filtrate was reconcentrated to give a brown oil. Purification by flash chromatography on silica gel eluting with n-hexane/ethyl acetate mixtures gave two major products.

The more polar product, N-acetyl-3,5,8,9,11,35,2',4'-nona-O-triethylsilyl-13,14-anhydroamphotericin B (E4) has: $\nu$max (thin film): 3428,2942,2900,2868,1731,1689,1669,1638,1512,1455,1408, 1372,1305,1234,1152,1070,1002,935,920 cm$^{-1}$; $\delta$H(400MHz) [(CD3)2CO]: 6.55–6.11 (13H, series of m), 5.98 (1H,dd, J 15.2 and 6.0 Hz), 5.55 (1H,dd, J 14.8 and 9.4 Hz), 4.80 (1H,d, J 8.8 Hz) 4.71–4 63 (2H,m), 4.62(1H,s), 4.59(1H,s), 4.28(1H,m), 4.20(1H,m), 4.11(1H,m), 4.01(1H,m), 3.96–3.84 (3H,m), 3.73 (2H,m), 3.51 (1H,t, J 8.9 Hz), 3.35 (1H,dq, J 8.5 and 6.2 Hz), 2.64 (1H,dd, J 10.9 and 8.7 Hz), 2.58–2.55 (2H,m), 2.43 (1H,m), 2.38–2.30 (1H,m), 2.21 (1H,m) 2.20–1.85 (7H,m, including S at 1.99), 1.82–1.44 (6H, series of m), 1.25 (3H,d, J 6.1 Hz) 1.18 (3H,d, J 6.0 Hz), 1.12–0.85 (87H, broad, complex) 0.77–0.54 (54H, broad, complex) ppm.

Mass spectrum FAB (3-NOBA/Na matrix) M=2020 relative intensity 63%, 1997 relative intensity 36%. 1821 (80%), 1822 (100%). Hplc: Normal phase - Waters Z model radially compressed silica column. Eluent 50% ethyl acetate in n-hexane—Flow rate 2ml/min, detection at 406 nm. Retention time=13.0 minutes.

Method B

The compound of Description 1 (527 mg, 0.530 mmol) was suspended in dry dichloromethane (20 ml) at 0° under nitrogen when 2,6-lutidine (0.956 g, 1.04 ml, 8.9 mmol) followed by triethylsilyl trifluoromethanesulphonate (1.82 g, 1.56 ml, 6.9 mmol) were added via syringe. After stirring for 0.5 hours, the mixture was poured into a mixture of diethyl ether/ice/1N hydrochloric acid. The aqueous layer was separated, extracted with diethyl ether and the combined organic extracts washed with ice-cold 1N hydrochloric acid, dried over anhydrous sodium sulphate, filtered and evaporated in vacuo to give a brown oil. Column chromatography on silica gel eluting with n-hexane/ethyl acetate mixtures gave N-acetyl-3,5,8,9,11,15,35,2',4'-nona-O-triethylsilyl-13,14-anhydroamphotericin B (E4) as in Method A.

EXAMPLE 5

N-Acetyl-13,14-anhydroamphotericin B methyl ester (E5)

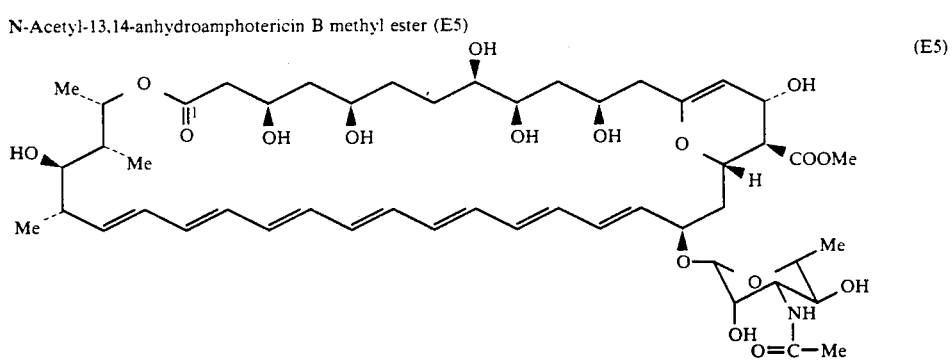
(E5)

To a slurry of N-acetyl amphotericin B methyl ester (0.36 g, 0.36 mmol) in dry methylene chloride (5 ml) and 2,6-lutidine (0.9 ml, 7.92 mmol), under nitrogen at 0° C., was added trimethylsilyl trifluoromethanesulphonate (1.1 ml, 5.76mmol). After stirring for 0.3 hours the reaction was evaporated in vacuo and the residue was taken up in n-hexane (250 ml). The precipitate was removed by filtration and the hexane was evaporated. The silylated product was purified by flash chromatography on silica-gel using ethyl acetate/n-hexane mixtures.

The silylated product was dissolved in dry tetrahydrofuran (5ml) in a plastic bottle. Under nitrogen, hydrogen fluoride-pyridine solution (5.5ml of a solution made from 14.64 g of 70% hydrogen fluoride-pyridine reagent and 92 ml of pyridine and made up to 250 ml with tetrahydrofuran - equivalent to 2M HF-11 mmol)

was added with a plastic syringe. After stirring for 1 hour the solution was poured into diethyl ether: n-hexane (800 ml, 1:1) and the precipitate was filtered and washed with diethyl ether, ethyl acetate and diethyl ether and dried.

By 'H-NMR this material was not totally desilylated. The solid was dissolved in the minimum of dry tetrahydrofuran in a plastic bottle. Under nitrogen, hydrogen fluoride-pyridine solution (5.5 ml of a solution made from 14.64 g of 70% hydrogen fluoride, pyridine reagent and 92 ml of pyridine and made up to 250 ml with tetrahydrofuran—equivalent to 2M in HF—11 mmol) was added with a plastic syringe. After stirring for 4.5 hours the reaction was poured into diethyl ether/n-hexane (800 ml, 1:1) and the precipitate was filtered and washed with diethyl ether, ethyl acetate and diethyl ether and dried to give the title compound (E5).

δH 400MHz (1:1 d$_5$ pyridine: d$_4$ methanol): 6.53-6.29 (12H, series of m), 6.06 (1H,dd,J 14.1 and 7.8Hz), 5.59 (1H,dd,J 14.3 and 9.8Hz), 5.49 (1H,m), 4.92 (1H,d,J 1.9Hz), 4.80-4.75 (3H, series of m), 4.50-4.40 (2H, series of m), 4.32-4.23 (2H, series of m), 4.16 (1H,dd, J 3.0 and 0.9Hz), 3.97 (1H,m), 3.88 (1H,m), 3.79 (3H,s), 3.73 (1H,m), 3.54 (1H,m), 3.45-3.35 (3H, series of m), 2.83 (1H,dd,J 10.8 and 9.0Hz), 2.57-2.44 (2H, series of m), 2.36-2.09 (6H, series of m), 2.07 (3H,s), 2.03-1.73 (3H, series of m), 1.70-1.50 (5H, series of m), 1.44 (3H,d,J 6.1Hz), 1.34 (3H,d,J 6.4Hz), 1.24 (3H,d,J 6.5Hz) and 1.15 (3H,d,J 7.1Hz)ppm.

IR νmax (KBr disc): 1727, 1656 and 1532 cm$^{-1}$ UV λmax (methanol): 406, 382, 363 and 345 nm Mass spectrum: FAB (Thioglycerol/thiodiethanol/Na matrix) observed mass MNa$^+$ 984.5, calculated for C$_{50}$H$_{75}$NO$_{17}$961.50.

EXAMPLE 6

45.9 mmol) under nitrogen at room temperature. Trimethylsilyl trifluoromethanesulphonate (6.8 ml, 35.1 mmol) was added and the reaction allowed to stir for 0.5 hours. The reaction was then evaporated in vacuo. The residue was taken up in n-hexane (800 ml), filtered to remove the precipitate and the filtrate evaporated to give the product.

The crude product was dissolved in dry tetrahydrofuran (20 ml) and transferred into a plastic bottle. Under nitrogen, hydrogen fluoride.pyridine solution (72 ml of a solution made from 14.64 g of 70% hydrogen fluoride.pyridine reagent and 92 ml of pyridine made up to 250 ml with tetrahydrofuran -equivalent to 2M HF—0.144 mmol) was added with a plastic syringe.

The reaction was stirred for 1 hour then poured into 1:1 diethyl ether/hexane (2L). The precipitate was filtered and washed with diethyl ether, ethyl acetate and diethyl ether. The solid was reslurried in saturated sodium bicarbonate, filtered, washed with water, dissolved in the minimum of dimethylsulphoxide, diluted with methanol and poured into diethyl ether (1L). The preciptate was filtered, washed with diethyl ether, ethyl acetate and diethyl ether and dried to give the title compound (E6).

νmax (KBr disc):1700, 1650, 1555 cm$^{-1}$. Mass Spectrum: FAB (THIOGLYCEROL Matrix) observed mass. (MH$^+$) 906—calculated mass (M$^+$) 905.48.

Method B

To a solution of N-(9-fluorenylmethoxycarbonyl)-13,14-anhydro-amphotericin B (E7) (89 mg, 0.08 mmol) in dimethylsulphoxide/methanol (3:1, 3 ml) under nitrogen was added piperidine (10 μl, 0.1 mmol). The reaction was stirred for 2 hours, diluted with methanol (1 ml) and precipitated in diethyl ether (500 ml). The solid was filtered, washed with diethyl ether and dried to 13,14-Anhydroamphotericin B (E6)

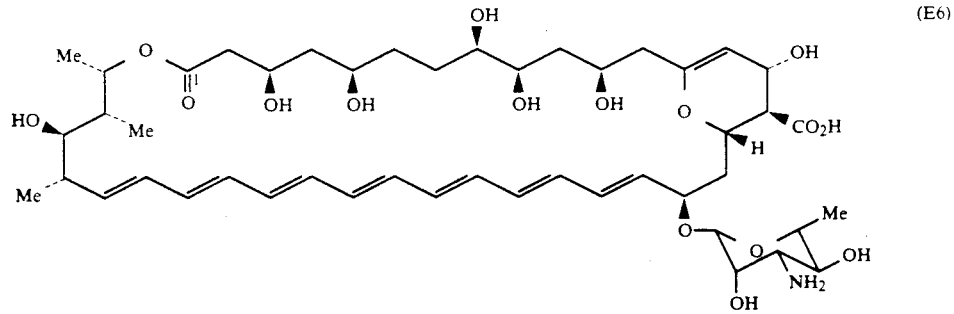

Method A

Amphotericin B (1.66 g, 1.8 mmol) was slurried in dry methylene chloride (20 ml) with 2,6-lutidine (5.3 ml, give the title compound (E6).

EXAMPLE 7

N-(9-Fluorenylmethoxycarbonyl)-13,14-anhydroamphotericin B (E7)

-continued

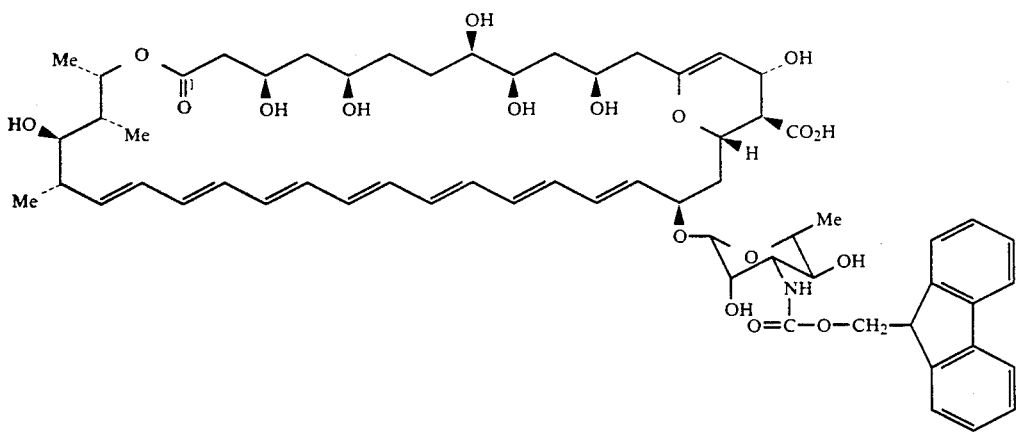

(E7)

N-(9-Fluorenylmethoxycarbonyl)amphotericin B (D2) (1 g, 0.87 mmol) was slurried in dry methylene chloride (9 ml) and 2,6-lutidine (1.73 ml, 14.8 mmol). Trimethylsilyl trifluoromethanesulphonate (2.19 ml, 11.3 mmol) was added under nitrogen and at 0° C. After stirring for 0.3 hours the reaction was evaporated in vacuo. The residue was taken up in n-hexane (1L), filtered and evaporated to give a gum.

Without further purification the gum (1.55 g) was dissolved in dry tetrahydrofuran (12 ml), transferred to a plastic bottle and, under nitrogen, treated with hydrogen fluoride.pyridine solution (52 ml of a solution made from 2.4 g of 70% hydrogen fluoride.pyridine reagent and 12.8 ml of pyridine and made up to 63 ml with tetrahydrofuran—equivalent to 1.33M HF—69 mmol). After stirring for 4 hours the solution was poured into diethyl ether (8L) and filtered. The precipitate was washed with diethyl ether, dried and purified on reverse phase silica gel using methanol/water mixtures to give the title compound (E7).

EXAMPLE 8

N-(9-Fluorenylmethoxycarbonyl)-3.5.8.9.11.15.35.2'.4'-nona-O-trimethylsislyl-13.14-anhydroamphotericin B methyl ester (E8).

To a slurry of N-(9-fluorenylmethoxycarbonyl) amphotericin B methyl ester (D3) (0.17 g, 0.15 mmol) in dry methylene chloride (1.5 ml) under nitrogen was added 2,6-lutidine (0.29 ml, 2.5 mmol) followed by trimethylsilyl trifluoromethanesulphonate (0.37 ml, 1.95 mmol). After stirring at room temperature for 0.25 hours, the solution was evaporated and n-hexane (60 ml) added. The solids were triturated and removed by filtration. The organics were evaporated to give the title compound (E8). δH270MHz ((CD3)2CO): 7.87 (2H,d,J 4.2Hz), 7.70 (2H, m), 7.42 (2H,t,J 7.7Hz), 7.32 (2H,m), 6.36 (12H,m) 5.90 (1H,dd), 5.61 (1H.dd), 4.91 (1H,m), 4.75–4.38 (3H, series of m), 4.57 (1H,s), 4.50 (1H,s), 4.39–4.09 (4H series of m), 4.09–3.78 (4H, series of m), 3.76 (3H,s), 3.63 (1H,m) 3.46 (1H,t), 3.30 (1H,m), 2.63–2.28 (5H, series of m), 2.13 (1H.d), 2.03–1.78 (5H, series of m), 1.78–1.35 (9H, series of m), 1.21 (3H.d), 1.17 (3H,d), 1.03 (3H,d), 0.97 (3H,d) and 0.13 (81H, series of m) ppm.

IR νmax (CH2Cl2): 1730 cm$^{-1}$ UV λmax (hexane) : 402, 380, 362 nm. Mass spectrum : FAB (3-NOBA/Na matrix) observed mass MNa+1813, calculated for $C_{90}H_{155}NO_{18}Si_9$ 1789.92.

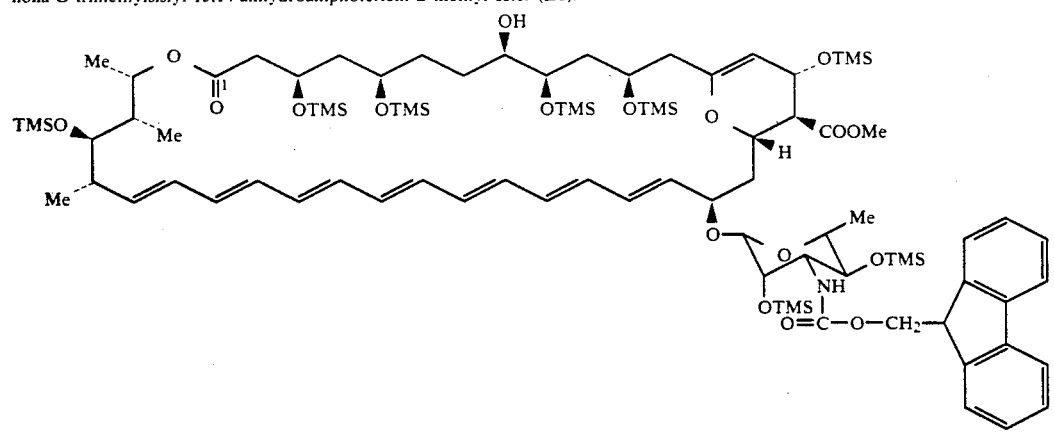

(E8)

EXAMPLE 9

N-(9-Fluorenylmethoxycarbonyl)-13.14-anhydroamphotericin B methyl ester (E9)

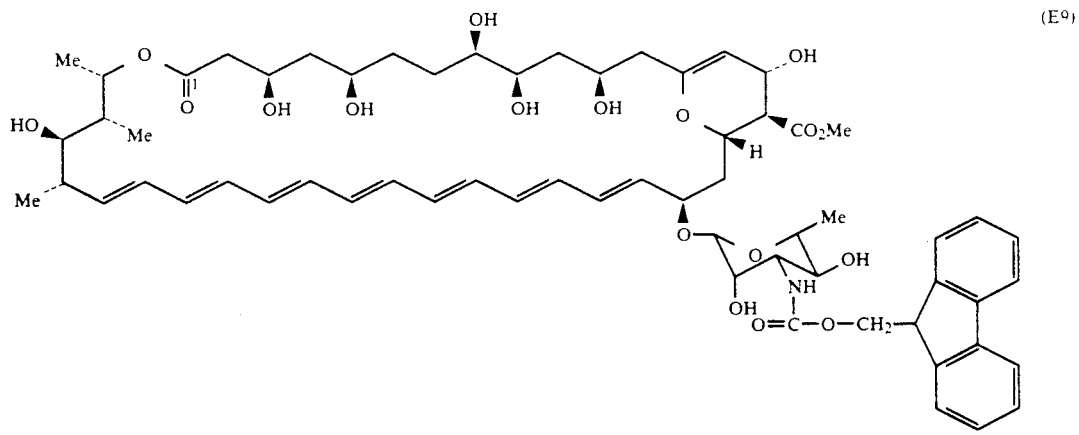

(E9)

To N-(9-fluorenylmethoxycarbonyl)-3,5,8,9,11,15,35,2',4'-nona-O-trimethylsilyl-13,14-anhydroamphotericin B methyl ester (EB) (0.77 g. 0.42 mmol) in dry tetrahydrofuran (10 ml) under nitrogen in a plastic bottle was added, with a plastic syringe, hydrogen fluoride.pyridine solution (26 ml of a solution made from 8.5 g of 70% hydrogen fluoride.pyridine reagent and 45 ml of pyridine in 180 ml of tetrahydrofuran equivalent to 1.3M HF—34 mmol). After stirring for 4 hours, the solution was poured into a 1:1 mixture of diethyl ether/n-hexane (2L). The precipitate was filtered and washed with diethyl ether, saturated sodium bicarbonate solution and water and dried to give the title compound (E9). The compound was purified by silica-gel chromatography using methylene chloride/methanol mixtures under medium pressure.

$\delta$H400MHz (1:1 $d_5$ pyridine:$d_4$ methanol): 7.84 (2H,d, J 7.5Hz), 7.72 (2H,d,J 7.2Hz), 7.42 (2H,t,J 7.4Hz), 7.31 (2H,t, J 7.4Hz), 6.55–6.30 (12H, complex), 6.07 (1H,dd, J 14.1 and 7.6 Hz), 5.60 (1H,dd,J 13.9 and 9.8Hz), 5.47 (1H,m), 4.92 (1H,m) 4.81–4.71 (3H,complex), 4.50–4.41 (2H, complex), 4.38 (2H,d,J 7.2Hz), 4.3–4.2 (2H, complex), 4.21 (1H,m), 4.05 (1H,dd, J 10.2 and 2.8Hz), 3.95 (1H,t,J 9.6Hz), 3.86 (1H,d,J 9.6Hz), 3.78 (3H,s), 3.75 (1H,m), 3.56 (1H,m), 3.44 (1H,m), 3.42 (1H,m), 2.82 (1H,dd J 10.5 and 9.3 Hz), 2.55 (1H,m), 2.48 (1H,dd,J 17.1 and 9.7Hz), 2.33 (1H,m), 2.29 (2H,m), 2.18 (2H,m), 2.12 (1H,m), 1.98 (2H, complex), 1.80 (1H.m), 1.7–1.5 (4H, complex), 1.52 (1H,m), 1.47 (3H,d,J 6.1Hz), 1.34 (3H,d,J 6.4Hz), 1.25 (3H,d,J 6.5Hz) and 1.15 (3H,d,J 7.1Hz) ppm.

IR $\nu$max (nujol): 1720 cm$^{-1}$ UV $\lambda$max (ethanol) : 407, 384, 365 nm Mass spectrum: FAB (3-NOBA/Na matrix) observed mass MNa$^+$ 1164, calculated for $C_{63}H_{83}NO_{18}$ 1141.56.

EXAMPLE 10

13,14-Anhydroamphotericin B methyl ester (E10)

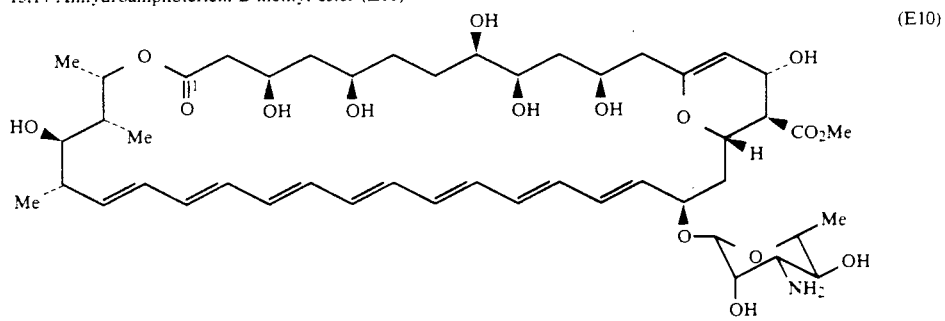

(E10)

N-(9-(Fluorenylmethyoxycarbonyl)-13,14-anhydro amphotericin B methyl ester (E9) (0.2 g, 0.18 mmol) was dissolved in dimethylsulphoxide:methanol (2 ml,3:1). Under nitrogen, piperidine (18 $\mu$l, 0.23 mmol) was added and after stirring for 3 hours, the solution was poured into diethyl ether (200 ml). The precipitate was filtered and washed with diethyl ether, ethyl acetate/diethyl ether and diethyl ether and dried to give the title compound (E10).

IR $\nu$max (KBr disc): 1725, 1675, 1645, 1600 cm$^{-1}$. Mass spectrum: FAB (THIOGLYCEROL matrix) observed mass MH$^+$ 920, calculated for $C_{48}H_{73}NO_{16}$ 919.49.

EXAMPLE 11

N-(9-Fluorenylmethoxycarbonyl)-16-decarboxy-16-hydroxymethyl-13,14-anhydroamphotercin B (E11)

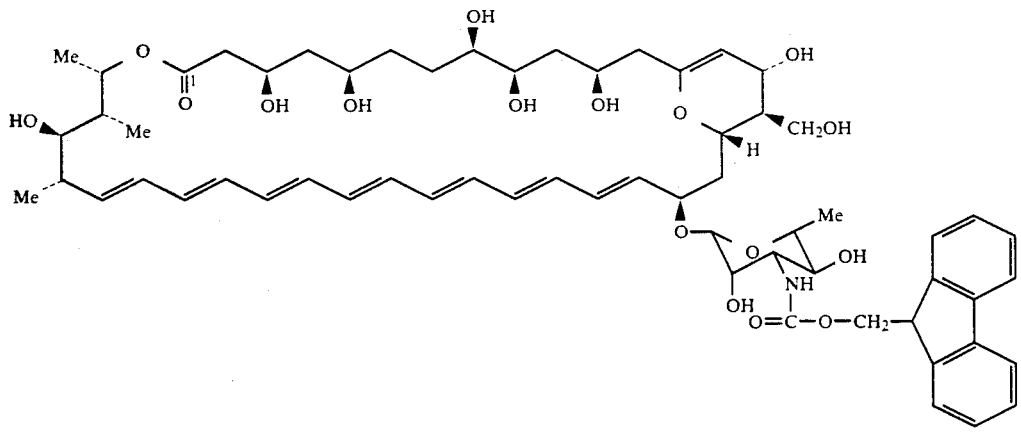

To a solution of N-(9-fluorenylmethoxycarbonyl)-13,14-anhydroamphotericin B methyl ester (E9) (0.70 g, 0.61 mmol) in methanol/tetrahydrofuran (15 ml, 3:1) at room temperature was added portionwise sodium borohydride (0.58 g, 15.3 mmol).

After 0.3 hours the reaction was quenched by adding saturated sodium bicarbonate solution (1 ml) and then poured into saturated sodium bicarbonate solution (800 ml). The precipitate was filtered and washed with water to neutrality and dried to give the title compound. (E11).

Mass spectrum: FAB (3-NOBA/Na matrix) observed mass MNa+ 1136, calculated for $C_{62}H_{83}NO_{17}$ 1113.57.

EXAMPLE 12

To a solution of N-(9-fluorenylmethoxycarbonyl)-16-decarboxy-16-hydroxymethyl-13,14-anhydroamphotericin B (E11) (0.13 g, 0.11 mmol) in dimethylsulphoxide/methanol (3 ml;3:1) under nitrogen was added piperidine (22 μl, 0.22 mmol). After stirring for 1.5 hours, the solution was poured into diethyl ether (200 ml). The precipitate was filtered and washed thoroughly with diethyl ether and dried to give the title compound (E12).

IR νmax (nujol): 1710 and 1680 cm$^{-1}$. UV λmax (methanol): 406, 383, 363 nm. Mass spectrum: FAB (3-NOBA/Na matrix) observed mass MNa+ 914, calculated for $C_{47}H_{73}NO_{15}$ 891.50.

EXAMPLE 13

16-Decarboxy-16-hydroxymethyl-13,14-anhydroamphotericin B (E12)

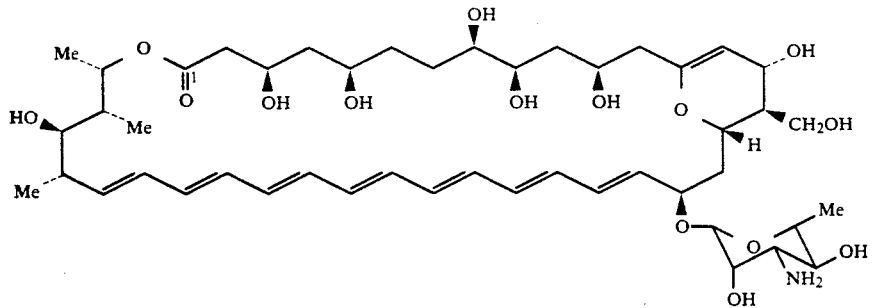

N-(9-fluorenylmethoxycarbonyl)-3,5,8,9,11,15,35,2',4'-nona-O-triethylsilyl-13,14-anhydroamphotericin B methyl ester (E13)

-continued

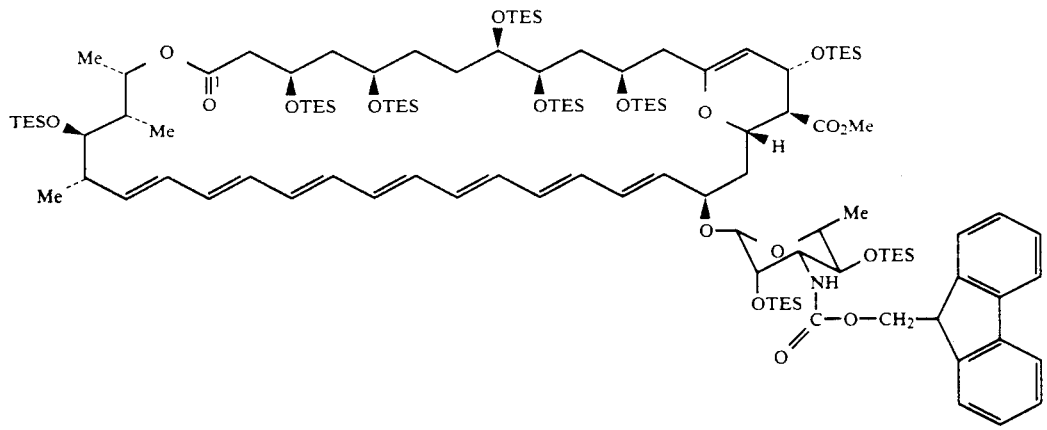
(E13)

Under nitrogen, N-(9-fluorenylmethoxycarbonyl)-13,14-anhydroamphotericin B methyl ester (E9) (3.18 g, 2.7 mmol) was slurried in dry methylene chloride (25 ml) and 2,6-lutidine (5.73 ml, 48.6 mmol). At room temperature, triethylsilyl trifluoromethanesulphonate (8.1 ml, 35.1 mmol) was added. After 0.75 hours the volatiles were removed in vacuo and the residue taken up in n-hexane (1L). The precipitate was removed by filtration and the filtrate evaporated.

The product was purified by flash chromatography on silica-gel using ethyl acetate/n-hexane mixtures, to give the title compound (E13).

UV λmax (hexane): 407,383,363,345,265,206 nm. Mass spectrum: FAB (3-NOBA matrix) observed mass MH⁻ 2169, calculated for $C_{117}H_{209}NO_{18}Si_9$ 2168.34.

EXAMPLE 14

40 minutes, the mixture was poured into diethyl ether-/ice cold 0.2M sodium bisulphate solution. The product was extracted into diethyl ether and the organic extracts were dried over anhydrous magnesium sulphate, filtered and evaporated in vacuo.

The crude product was stirred at 0° C. in dry diethyl ether (15 ml) and treated with triethylamine (106 mg, 0.15 ml, 1.04 mmol) followed by 2-thiopyridyl chloroformate (180 mg, 5.3 ml of 34 mg/ml solution in dichloromethane, 1.04 mmol). After stirring at 0° C. for 30 minutes, the mixture was diluted with diethyl ether (50 ml), dried over anhydrous magnesium sulphate, filtered and evaporated in vacuo. Purification by flash chromatography on silica gel eluting with n-hexane/ethyl acetate mixtures gave a mixture, containing title compound (E14) as a yellow foam.

HPLC. Normal phase—Waters radially compressed

N-Acetyl-3,5,8,9,11,15,35,2',2'-nona-O-triethylsilyl-13,14-anhydroamphotericin B (2-pyridylthio) ester (E14)

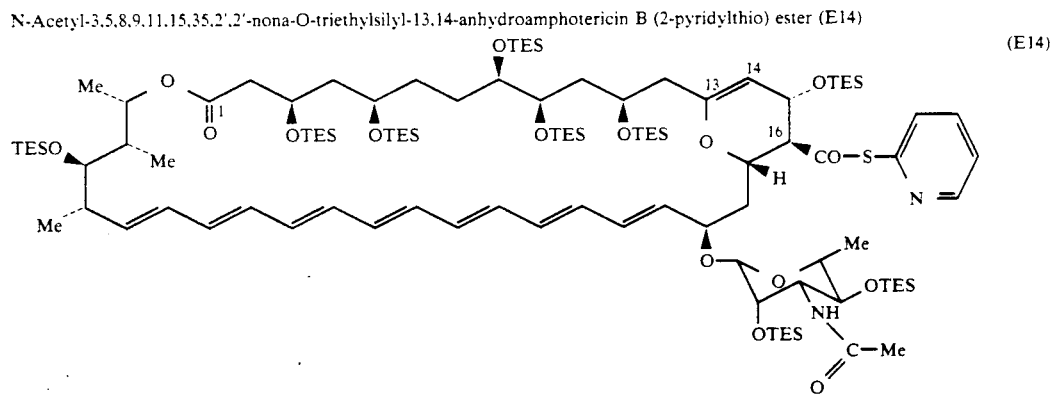
(E14)

N-Acetyl-13-O-methylamphotericin B (D1) (0.94 g, 0.95 mmol) was suspended in dry dichloromethane (50 ml) at 0° C. under a nitrogen atmosphere and 2,6-lutidine (1.98 g, 2.15 ml, 18.50 mmol) followed by triethylsilyl trifluoromethanesulphonate (3.76 g, 3.22 ml, 14.00 mmol) were added via syringe. After stirring at 0° C. for silica column. Eluent 15% ethyl acetate in n-hexane-2 ml/min. Detection wavelength 406 nm.

Retention time of 13,14-anhydro product: 7.0 minutes.

EXAMPLE 15

N-Acetyl-16-acetyl-16-decarboxy-3,5,8,9,11,15,35,2',4'-nona-O-triethylsilyl-13,14-anhydroamphotericin B (E15)

-continued

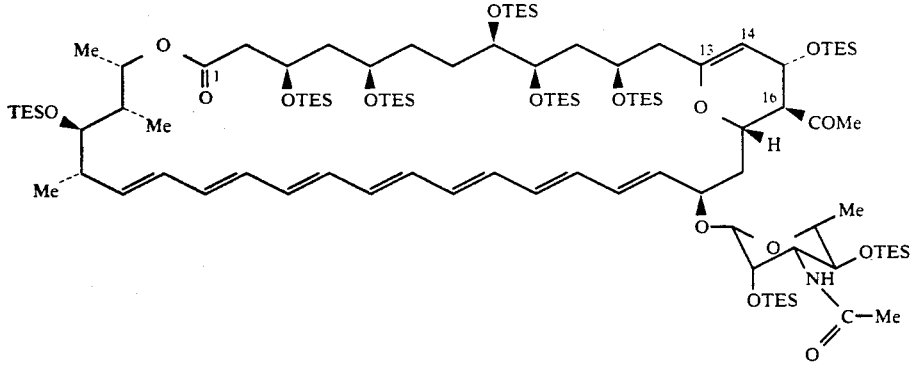
(E15)

The product mixture of Example 14 was stirred at 0° C. in dry tetrahydrofuran (5 ml) under a nitrogen atmosphere and methyl magnesium bromide (0.37 ml of 3M solution in diethyl ether, 1.1lmmol) was added via syringe. After 15 minutes at 0° C. a further 0.37 ml of methylmagnesium bromide solution was added and the mixture was stirred for a further 10 minutes at 0° C. The mixture was poured into diethyl ether/water and the product was extracted into diethyl ether. The combined organic extracts were dried over anhydrous magnesium sulphate, filtered and concentrated in vacuo. Purification by flash chromatography on silica gel—eluting with 4% diethyl ether in dichloromethane gave a mixture containing the title compound (E15).

HPLC. Normal phase-conditions as in Example 14. Retention time of 13,14-anhydro product: 3.6 minutes.

EXAMPLE 16

The fractions containing the 13,14-anhydro product were washed with ice/0.2M sodium hydrogen sulphate solution to remove lutidine, dried over anhydrous magnesium sulphate, filtered and evaporated.

Rf 0.40 (silica)-25% ethyl acetate in n-hexane. δH 400MHz (($CD_3$)$_2$CO) 7.88(2H, d, J 7.5Hz), 7.70(2H, d, J 7.5Hz), 7.43(2H, t, J 7.4Hz), 7.34(2H, t, J 7.4Hz), 6.56–6.11(12H, series of m), 5.99(1H, dd, J 6.0, 15.4Hz), 5.55(1H, dd, J 9.4, 14.9Hz), 5.34(1H, d, J 9.9Hz), 4.80(1H, d, J 8.7Hz), 4.73–4.60(2H, m), 4.63(1H, s), 4.59(1H, s), 4.50(1H, dd, J 6.5, 10.4Hz), 4.35(1H, dd, J 6.5, 10.4Hz), 4.32–4.17(3H, m), 4.12((1H, m), 4.01(1H, m), 3.90(1H, d, J 2.7Hz) 3.85(1H, dd, J 2.8, 8.7Hz), 3.80–3.66(2H, m), 3.61(1H, dt, J 2.7, 9.7Hz), 3.45(1H, t, J 9.1Hz), 3.34(1H, m), 2.64(1H, dd, J 8.7, 10.8Hz), 2.61–2.50(2H, m), 2.43(1H, m), 2.40–2.28(1H, m), 2.24–2.15(1H, m), 2.08–1.88(5H, series of m), 1.83–1.47(6H, series of m), 1.25(3H, d, J 6.1Hz), N-(9-Fluorenylmethoxycarbonyl)-3,5,8,9,11,15,35,2',4'-nona-O-triethylsilyl-13,14-anhydroamphotericin B (E16)

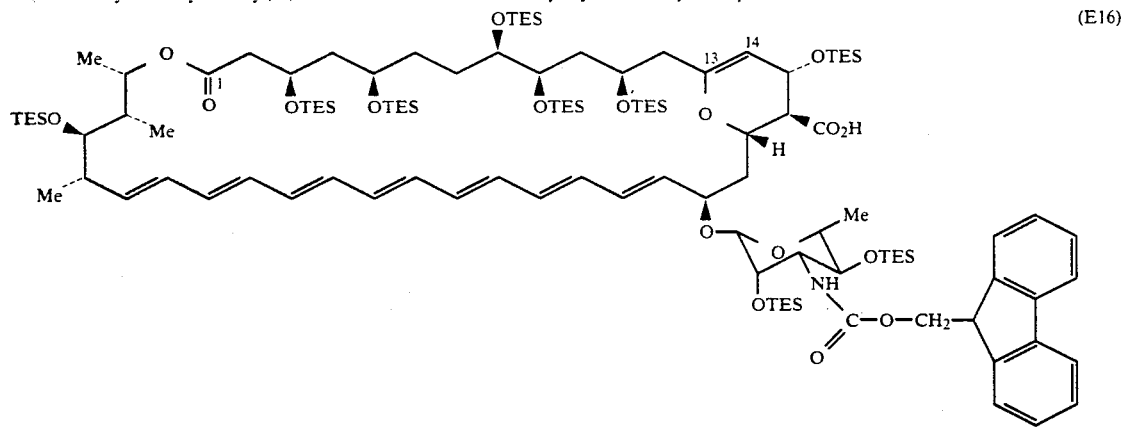
(E16)

The product of Description 4 (1.52 g) was suspended in dry dichloromethane (60 ml) at 0° C. under nitrogen and 2,6-lutidine (2.55 g, 2.76 ml, 23.80 mmol) followed by triethylsilyl trifluoromethanesulphonate (4.89 g, 4.18 ml, 18.50 mmol) were added via syringe. After stirring at 0° C. for 30 minutes the solvent was evaporated and the residue was dissolved in n-hexane, filtered and the filtrate was reconcentrated to give a brown oil. Purification by column chromatography on silica gel eluting with n-hexane/ethyl acetate mixtures gave the title product (E16).

1.18(3H, d, J 6.0Hz), 1.10–0.88(87H, series of m), 0.77–0.56(54H, series of m)ppm. The carboxylic acid proton was not observed.

IR νmax (thin film): 3445, 3500-2500 (broad, weak), 1737 (shoulder at 1720), 1680, 1510, 1461, 1416, 1380, 1310, 1240, 1192, 1169, 1080, 1007, 977, 740, 672 cm$^{-1}$.

Mass spectrum: FAB (3-NOBA matrix) Observed mass MH$^+$ 2155.5. Calculated for $C_{116}H_{207}NO_{18}Si_9H^+$ 2155.

EXAMPLE 17

N-(9-Fluorenylmethoxycarbonyl)-3,5,8,9,11,15,35,2',4'-nona-O-triethylsilyl-13,14-anhydroamphotericin B (2-pyridylthio)ester (E17)

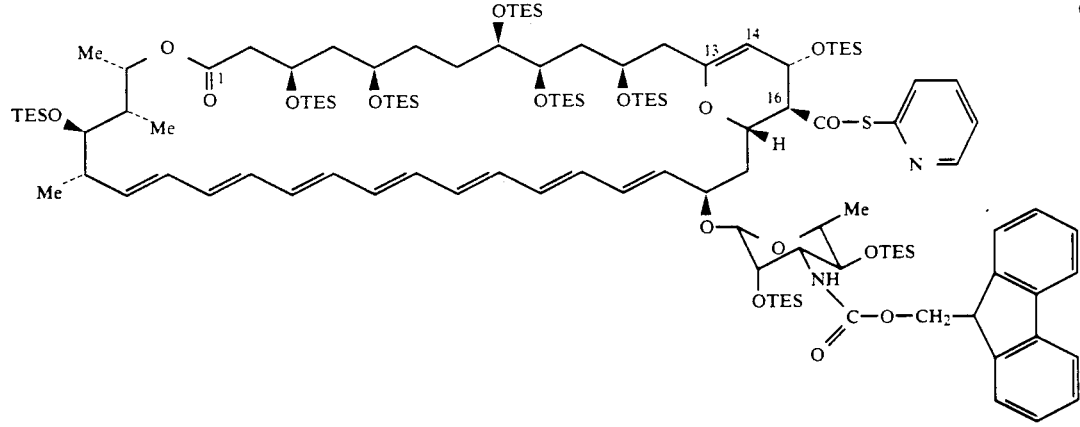

(E17)

N-(9-Fluorenylmethoxycarbonyl)-3,5,8,9,11,15,35,2',4'-nona-O-triethylsilyl-13,14-anhydroamphotericin B (E16) (460 mg, 0.21 mmol) was treated at 0° C. with triethylamine (24 mg, 0.03 ml, 0.24 mmol) followed by 2-thiopyridyl chloroformate (52 mg, 1.50 ml of 35 mg/ml solution in dichloromethane) in diethyl ether (12 ml). After stirring at 0° C. for 30 minutes, the mixture was diluted with diethyl ether, dried over anhydrous magnesium sulphate, filtered and evaporated in vacuo. Chromatographic purification gave the title compound (E17) as a yellow glassy solid.

Rf: 0.28(silica), 10% ethyl acetate in n-hexane. $\delta$H 270MHz ((CD$_3$)$_2$CO): 8.73(1H, d J 4Hz), 7.94(1H, dt, J 8, 2Hz), 7.88(2H, d, J 8Hz), 7.74(1H, d, J 8Hz), 7.71(2H, d J 8Hz), 7.50-7.27(5H, m), 6.65-6.15(12H, series of m), 6.0(1H, dd, J 15, 7Hz), 5.65(1H, dd, J 9, 14Hz), 5.32(1H, d, J 10Hz), 4.90-4.60(2H, m), 4.74(1H, s), 4.66(1H, s), 4.51(1H, dd, J 10, 7Hz), 4.40-3.65(10H, series of m), 3.93(1H, d, J 3Hz), 3.86(1H, dd, J 8, 2Hz), 3.50-3.35(2H, m), 3.03(1H, dd, J 11, 9Hz), 2.65-1.40(16H, series of m), 1.23(3H, d, J 6Hz), 1.18(3H, d, J 6Hz), 1.16-0.85(87H, series of m), 0.85-0.45(54H, series of m)ppm IR $\nu$max (thin film) : 3457, 3020, 2962, 2920, 2883, 1736, 1705, 1679, 1577, 1508, 1460, 1420, 1383, 1311, 1240, 1192, 1169, 1080, 1007, 836, 730 cm$^{-1}$. Mass spectrum: FAB(3-NOBA/Na matrix) observed mass MNa$^+$ 2270, calculated for C$_{121}$H$_{210}$N$_2$O$_{17}$Si$_9$S Na$^+$ 2270.

EXAMPLE 18

A mixture of N-(9-fluorenylmethoxycarbonyl)-3,5,8,9,11, 15,35,2',4'-nona-O-triethylsilyl-13,14-anhydroamphotericin B (2-pyridylthio) ester (E17) (282 mg, 0.13 mmol) and lithium borohydride (16.40 mg, 0.75 mmol) was stirred in dry tetrahydrofuran (10 ml) under nitrogen at room temperature. After 18 hours the mixture was cooled to −78° C., quenched with saturated ammonium chloride solution and allowed to reach room temperature. The product was extracted into diethyl ether and the combined extracts were dried over anhydrous magnesium sulphate, filtered and evaporated. Purification by flash chromatography on silica gel, eluting with 1-3% diethyl ether in dichloromethane gave the title compound (E18) as a yellow glass.

Rf: 0.40 (silica), 1% diethyl ether in dichloromethane. $\delta$H 270MHz ((CD$_3$)$_2$CO): 7.88(2H, d, J 7.4Hz), 7.70(2H, d, J 7.4Hz), 7.46-7.34(4H, m), 6.60-6.05(13H, series of m), 5.55(1H, dd, J 9, 14Hz), 5.39(1H, d, J 10.6Hz), 4.75-3.65(18H, series of m, including 4.73(1H,s), 4.65(1H, d, J 2Hz), 3.93(1H, d, J 3Hz)), 3.60(1H, dt, J 3.0, 9.5Hz), 3.46(1H, t, J 9.0Hz), 3.31(1H, m) 2.58(2H, m), 2,50-1.45(15H, series of m), 1.25(3H, d, J 6.1Hz), 1.18(3H, d, J 6.7Hz), 1.15-0.80(87H, series of m), 0.75-0.45(54H, series of m)ppm. The OH proton was not observed.

IR $\nu_{max}$ (thin film): 3600-3300 (broad, weak), 3440, 2950, 2902, 2870, 1726, 1668, 1505, 1455, 1408, 1372, 1302, 1233, 1187, 1161, 1073, 1000, 898, 857, 833, 805, 732, 720, 667 cm$^{-1}$. Mass spectrum: FAB(3-NOBA/Na N-(9-Fluorenylmethoxycarbonyl)-16-decarboxy-16-hydroxymethyl-3,5,8,9,11,15,35,2',4'-nona-O-triethylsilyl-13,14-anhydroamphotericin B (E18)

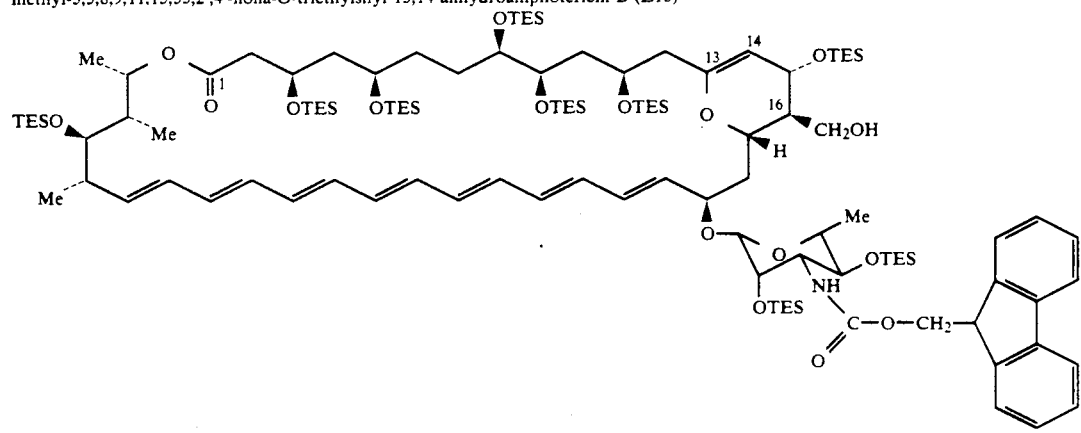

(E18)

matrix) observed mass MNa+ 2163, calculated for $C_{116}H_{209}NO_{17}Si_9Na^+$ 2163.

EXAMPLE 19

N-Trifluoroacetyl-3,5,8,9,11,15,35,2',4'-nona-O-triethylsilyl-13,14-anhydroamphotericin B (E19)

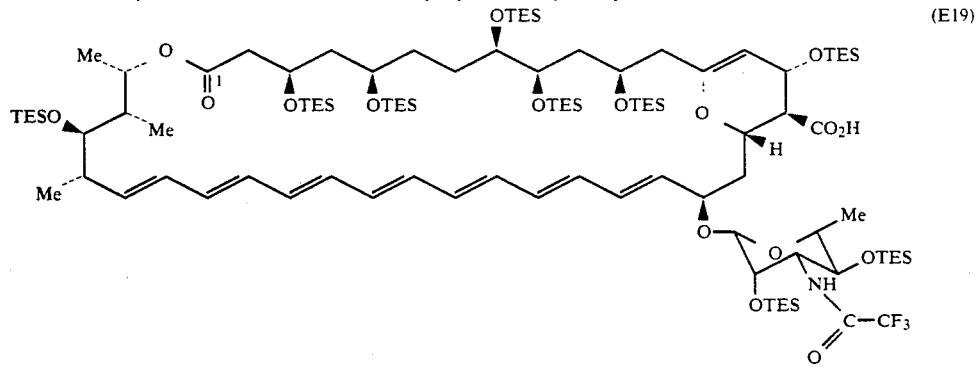

(E19)

N-Trifluoroacetylamphotericin B (D5) (1.99 g, 1.96 mmol) and d-10-camphorsulphonic acid (180 mg, 0.77 mmol) were stirred in dry tetrahydrofuran (10 ml)/methanol (60 ml) at room temperature under nitrogen. After 15 minutes, triethylamine (118 mg, 0.16 ml, 1.16 mmol) was added, the solution was concentrated to ca. 10 ml and added to diethylether (2L). The precipitated product was collected by filtration, washed with diethyl ether and ethyl acetate and dried to give N-trifluoroacetyl-13-O-methylamphotericin B as a yellow powder. HPLC: conditions as in Description 5: Retention time 5.1 minutes. The yellow powder was suspended in dry dichloromethane (60 ml) at 0° C. under nitrogen and 2,6-lutidine (2.51 g, 2.72 ml, 23.40 mmol), followed by triethylsilyl trifluoromethanesulphonate (4.77 g, 4.08 ml, 18.00 mmol) were added via syringe. After stirring at 0° C. for 30 minutes the solvent was evaporated and the residue was dissolved in n-hexane, filtered and the filtrate was reconcentrated. Purification by column chromatography on silica gel eluting with n-hexane/ethyl acetate mixtures gave the title compound (E19). Rf 0.23 (silica)-10% ethyl acetate in n-hexane.

EXAMPLE 20

N-Trifluoroacetyl-3,5,8,9,11,15,35,2',4'-nona-O-triethylsilyl-13,14-anhydroamphotericin B (E19) (697 mg) was stirred at 0° C. in dry diethylether (10 ml) and treated with triethylamine (33 mg, 0.05 ml, 0.33 mmol) followed by 2-thiopyridyl chloroformate (77 mg, 2.2 ml of 35 mg/ml solution in dichloromethane, 0.44 mnol).

After stirring at 0° C. for 30 minutes another 0.01 ml of triethylamine and 0.5 ml of 2-thiopyridyl chloroformate solution were added and stirring was continued for a further 20 minutes. The mixture was diluted with diethyl ether (100 ml), dried over anyhydrous magnesium sulphate, filtered and evaporated. Purification by flash chromatography on silica gel eluting with 10% ethyl acetate in n-hexane gave the title compound (E20) as a yellow glassy solid.

Rf : 0.89 (silica)- 15% ethyl acetate in n-hexane. δH 400MHz ((CD₃)2CO): 8.72(1H, ddd, J 0.9, 1.9, 4.8Hz), 7.94(1H, dt, J 1.9, 7.7Hz), 7.74(1H, dt, J 0.9, 7.9Hz), 7.45(1H ddd, J 1.1, 4.8, 7.6Hz), 7.27(1H, d, J 9.2Hz), 6.55–6.11(12H, series of m), 6.01(1H, dd, J 6.4, 15.4Hz), 5.56(1H, dd, J 9.3, 14.8Hz), 4.83–4.79(1H, m), 4.82(1H, s), 4.77(1H, m), 4.69(1H, m), 4.67(1H, s), 4.35(1H, ddd, J 2.1, 7.4, 10.5Hz), 4.22(1H, m), 4.16–4.06(2H, m), 4.05(1H, d, J 3.1Hz), 4.01(1H, m), 3.85(1H, dd, J 2.8, 8.6Hz), 3.80–3.69(2H, m), 3.68(1H, t, J 8.9Hz), 3.52(1H, dq, J 6.2, 8.6Hz), 3.04(1H, dd, J 8.6, 10.7Hz), 2.58(1H, dd, J 5.8, 17.1Hz, A of ABX system), 2.52(1H, dd, J 7, 17.1Hz, B of ABX system), 2.43(1H, m), 2.40–2.30(2H, m), 2.12–1.88(5H, series of m), 1.82–1.58(5H, series of m), 1.51(1H, m), 1.27(3H, d, J 6.2Hz), 1.19(3H, d, J 6.0Hz), 1.10–0.92(87H, series of m), 0.77–0.59(54H, series of m)ppm.

IR $\nu_{max}$(thin film): 3430, 2958, 2916, 2880, 1737, 1703,

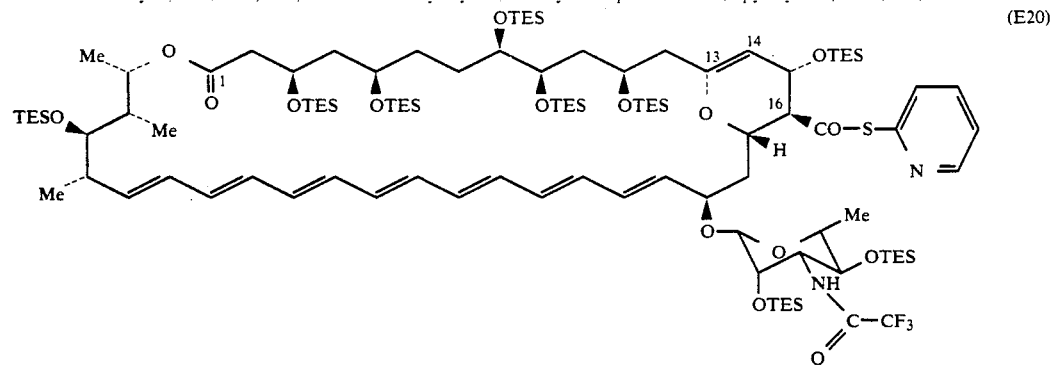

(E20)

1676, 1574, 1529, 1460, 1416, 1379, 1298, 1239, 1187, 1167, 1075, 1006, 837, 740, 672 cm⁻¹. Mass spectrum: FAB(3-NOBA/Na matrix) observed mass 2144, calculated for $C_{108}H_{199}N_2O_{16}Si_9SF_3Na^+$ 2144.

EXAMPLE 21 AND 22

N-Trifluoroacetyl-16-benzoyl-16-decarboxy-3,5,8,9,11,15,35,2',4'-nona-O-triethylsilyl-13,14-anhydroamphotericin B (E21) and 16-benzoyl-16-decarboxy-3,5,8,9,11,15,35,2',4'-nona-O-triethylsilyl-13,14-anhydroamphotericin B (E22)

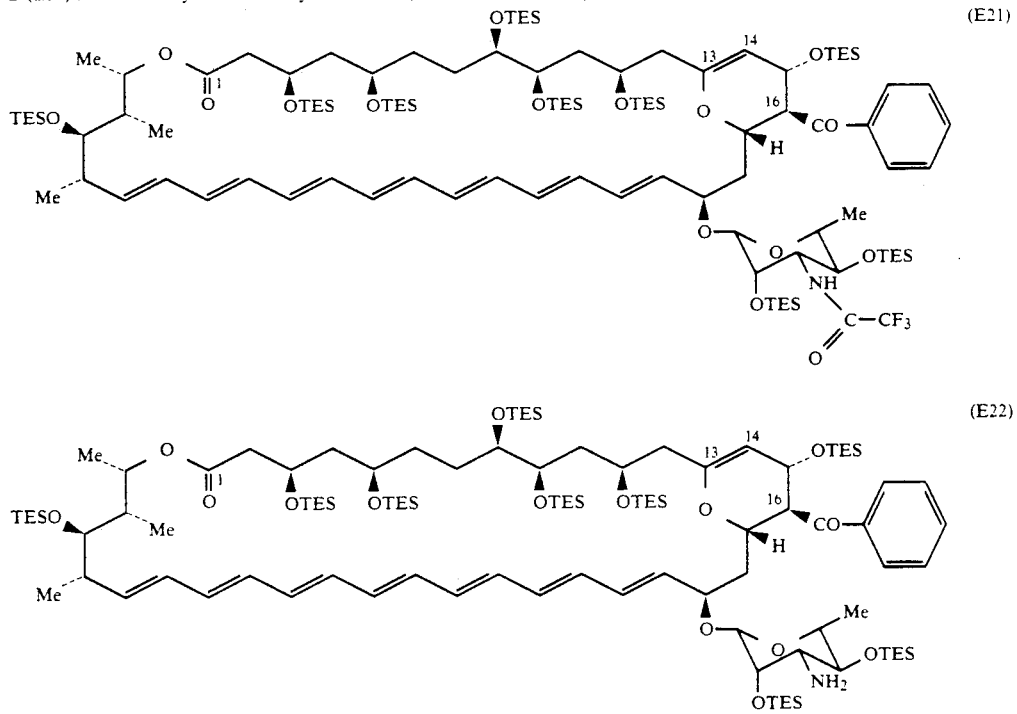

The pyridylthio ester of Example 20 (529 mg, 0.24 mmol) was stirred at 0° C. in dry tetrahydrofuran (15 ml) under nitrogen and phenylmagnesium bromide (0.79 ml) of 3M solution in diethyl ether, 2.35 mmol) was added via syringe. After 30 minutes another 0.30 ml of phenylmagnesium bromide solution was added and stirring was continued for a further 1.5 hours. Water was added and the product was extracted into diethyl ether. The combined extracts were washed with saturated brine, dried over anhydrous magnesium sulphate, filtered and evaporated. Purification by column chromatogrpahy on silica gel eluting with n-hexane/ethyl acetate and n-hexane/dichloromethane mixtures gave two major products.

The least polar N-trifluoroacetyl derivative (E21) has: Rf: 0.71 (silica), 15% ethyl acetate in n-hexane. δH 270MHz ((CD$_3$)$_2$CO): 8.12(2H, d, J 6.9Hz), 7.74–7.56(3H, m), 7.37(1H, d, J 9.1Hz), 6.57–6.09(12H, series of m), 5.90(1H, dd, J 6.6, 15.7Hz), 5.54(1H, dd, J 10, 15Hz), 4.83(1H, d, J 8.2Hz), 4.73(1H, s), 4.66(1H, m), 4.42(2H, m), 4.27–3.66(10H, series of m), 3.60(1H, t, J 8.9Hz), 3.05(1H, m), 2.66–2.33(4H, m), 2.10–1.43(12H, series of m), 1.23–0.88(93H, series of m), 0.88–0.35(54H, series of m)ppm. IR ν$_{max}$ (thin film): 3435, 2957, 2915, 2880, 1737, 1675, 1599, 1528, 1460, 1413, 1379, 1296, 1240, 1166, 1071, 1005, 897, 857, 839, 730, 670 cm$^{-1}$. Mass spectrum: FAB(3-NOBA/Na matrix) observed mass MNa$^+$ 2112±1, calculated for C$_{109}$H$_{200}$NO$_{16}$Si$_9$F$_3$Na$^+$ 2111.

The more polar free amino derivative (E22) has: Rf 0.38 (silica), 15% ethyl acetate in n-hexane. IR ν$_{max}$ (thin film): 2955, 2910, 2879, 1736, 1672, 1599, 1580, 1460, 1412, 1366, 1306, 1237, 1205, 1165, 1075 (broad), 1003, 974, 862, 837, 809, 736 cm$^{-1}$. Mass spectrum: FAB(3-NOBA/Na matrix) observed mass MNa$^+$ 2016±1, calculated for C$_{107}$H$_{201}$NO$_{15}$Si$_9$Na$^+$ 2015.3.

EXAMPLE 23

Rehydration of 13,14-anhydroamphotericin B (E6) to give amphotericin B 13,14-Anhydroamphotericin B (E6) (2.3 mg, 2.5×10$^{-6}$ moles) was dissolved in distilled water (3 ml). An aliquot of this solution (0.2 ml) was diluted with phosphate buffer at pH 2.4 (3 ml of 0.05M NaH$_2$PO$_4$ acidified using orthophosphoric acid).

The reaction was monitored by reverse phase HPLC. After 3.5 hours at room temperature, the starting material had been hydrated to give amphotericin B.

MIC Data

Method

The Minimum Inhibitory Concentration (MIC) was determined by diluting the test compound in a broth medium in a microtitre tray. The organisms, which had been grown previously in a broth medium (yeast nitrogen base + 1% glucose), were diluted and added to the wells to provide a final inoculum of approximately 10$^5$ colony-forming units per well. The trays were incubated at 37° C. and the turbidity of each well noted at intervals. The MIC was taken as the lowest concentration (in μg/ml) which prevented significant growth.

Results

| ORGANISM* | Minimum Inhibitory Concentration (μg/ml) (determined after 2 and 3 days incubation) | | | |
|---|---|---|---|---|
| | DAY | E6 | E10 | E12 |
| Candida albicans | 2 | 2 | 16 | 4 |
| 73/079 | 3 | 4 | 32 | 8 |
| Candida | 2 | 4 | 32 | 8 |
| parapsilosis | 3 | 8 | 32 | 16 |

-continued

| Minimum Inhibitory Concentration (μg/ml) (determined after 2 and 3 days incubation) | | | | |
|---|---|---|---|---|
| ORGANISM* | DAY | E6 | E10 | E12 |
| 937 A | | | | |

*Inoculum $10^5$ cells/ml

We claim:
1. A compound of formula (I), or a salt thereof:

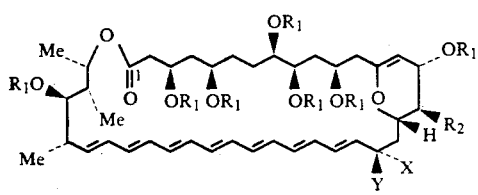

wherein:
each $R_1$ is independently hydrogen or a silyl protecting group selected from the group consisting of trimethylsilyl, triethylsilyl and tertiarybutyldimethylsilyl;
$R_2$ is a carboxyl group or a derivative thereof selected from the group consisting of hydroxycarbonyl, $C_{1-8}$ alkoxycarobnyl, phenyloxycarbonyl, naphthloxycarbonyl, heteroaryloxycarbonyl, $C_{1-8}$ alkylthiocarbonyl, phenylthiocarbonyl, naphthylthiocarbonyl, heteroarylthiocarbonyl, a primary, secondary, or tertiary amide in which the nitrogen moiety is optionally substituted with one or two $C_{1-6}$ alkyl groups; a $C_{1-6}$ alkyl, phenyl, naphthyl or heteroaryl ketone; or hydroxymethyl; any of said phenyl or naphthyl moieties optionally mono-, di-, or tri-substituted by substituents selected from the group consisting of carboxy, $C_{1-8}$ alkoxycarbonyl, hydroxy, $C_{1-8}$ alkyl, $C_{1-8}$ alkoxy, halogen and amino optionally mono- or di-substituted by $C_{1-8}$ alkyl;
said heteroaryl moiety is a 5- or 6-membered monocyclic or a 9- or 10-membered bicyclic heteroaryl containing one or two heteroatoms selected from the group consisting of nitrogen, oxygen and sulphur, which, in the case of more than one heteroatom, may be the same or different;
one of X and Y is hydrogen and the other is a sugar residue having the formula

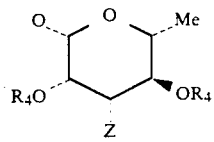

in which $R_4$ is independently hydrogen or a silyl protecting group as defined for $R_1$ above and Z is an amino group or a protected amino group $NHR_3$ wherein $R_3$ is selected from the group consisting of hydrogen, acetyl, trifluoroacetyl, 9-fluorenylmethoxycarbonyl, trichloroethoxycarbonyl, 2-methylsulphonylethoxycarbonyl and 2-trimethylsilylethoxycarbonyl; hydroxy; or
X and Y together with the carbon atom to which they are bonded are a carbonyl group; with the proviso that when each $R_1$ is trimethylsilyl and $R_2$ is methoxycarbonyl, one of X and Y is not hydroxy, 4-nitrophenylcarboxy or N-acetyl-3,4-o-trimethylsilymycosamine, or X and Y together with the carbon atom to which they are bonded are not a carbonyl group; when each $R_1$ is hydrogen and $R_2$ is methoxycarbonyl, one of X and Y is not hydroxy or 4-nitrophenylcarboxy; and when each $R_1$ is hydrogen and $R_2$ is carboxy, one of X and Y is not hydroxy.
2. A compound of formula (II), or a salt thereof.

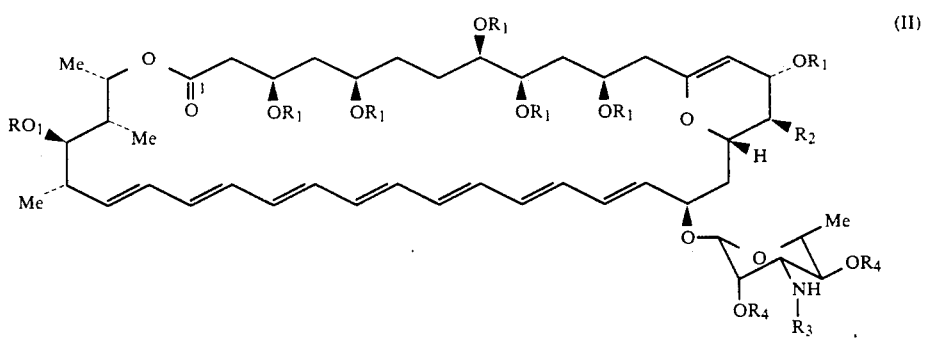

wherein $R_1$ and $R_2$ are as defined for formula (I) in claim 1, $R_3$ is hydrogen or an amine protection group selected from the group consisting of acetyl, trifluoroacetyl, 9-fluroenylmethoxycarbonyl, trichloroethoxycarbonyl, 2-methylsulphonylethoxycarbonyl and 2-trimethylsilylethoxycarbonyl and each $R_4$ is independently hydrogen or a silyl protecting group selected from the group consisting of trimethylsilyl, triethylsilyl and tertiarybutyldimethylsilyl, with the proviso that when each $R_1$ and $R_4$ are trimethylsilyl and $R_2$ is methoxycarbonyl, $R_3$ is not N-acetyl.
3. A compound according to claim 1 wherein $R_2$ is hydroxycarbonyl, methoxycarbonyl, hydroxymethyl, acetyl, benzoyl, or 2-pyridylthiocarbonyl.
4. A compound according to claim 2 wherein $R_3$ is hydrogen, acetyl, trifluoroacetyl, or 9-fluorenylmethoxycarbonyl.
5. A compound according to claim 2 wherein $R_4$ is hydrogen, trimethylsilyl or triethylsilyl.
6. A compound according to claim 2 wherein $R_1$ is hydrogen, trimethylsilyl or triethylsilyl; $R_2$ is hydroxycarbonyl, methoxycarbonyl, hydroxymethyl, acetyl, benzoyl or 2-pyridylthiocarbonyl; $R_3$ is hydrogen, acetyl, trifluoroacetyl or 9-fluorenylmethoxycarbonyl; and $R_4$ is hydrogen, trimethylsilyl or triethylsilyl.

7. A compound according to claim 1, wherein $R_1$ and $R_4$ are each hydrogen and Z is $NHR_3$, wherein $R_3$ is as defined by claim 1.

8. A compound according to claim 7 wherein $R_2$ is hydroxycarbonyl, methoxycarbonyl or hydroxymethyl; and $R_3$ is hydrogen, acetyl or 9-fluorenylmethoxycarbonyl.

9. A compound selected from the group consisting of:
N-acetyl-3,5,8,9,11,15,35,2',4'-nona-O-triethylsilyl-13,14-anhydroamphotericin B;
N-acetyl-13,14-anhydroamphotericin B methyl ester;
13,14-anhydroamphotericin B;
N-(9-fluorenylmethoxycarbonyl)-13,14-anhydroamphotericin B;
N-(9-fluorenylmethoxycarbonyl)-3,5,8,9,11,15,35,2',4'-nona-O-trimethylsilyl-13,14-anhydroamphotericin B methyl ester;
N-(9-fluorenylmethoxycarbonyl)-13,14-anhydroamphotericin B methyl ester;
13,14-anhydroamphotericin B methyl ester;
N-(9-fluorenylmethoxycarbonyl)-16-decarboxy-16-hydroxymethyl-13,14-anhydroamphotericin B;
16-decarboxy-16-hydroxymethyl-13,14-anhydroamphotericin B;
N-(9-fluorenylmethoxycarbonyl)-3,5,8,9,11,15,35,2',4'-nona-O-triethylsilyl-13,14-anhydroamphotericin B methyl ester;
N-acetyl-3,5,8,9,11,15,35,2',4'-nona-O-triethylsilyl-13,14-anhydroamphotericin B (2-pyridylthio) ester;
N-acetyl-16-acetyl-16-decarboxy-3,5,8,9,11,15,35,2',4'-nona-O-triethylsilyl-13,14-anhydroamphotericin B;
N-(9-fluorenylmethoxycarbonyl)-3,5,8,9,11,15,35,2',4'-nona-O-triethylsilyl-13,14-anhydroamphotericin B;
N-(9-fluorenylmethoxycarbonyl)-3,5,8,9,11,15,35,2',4'-nona-O-triethylsilyl-13,14-anhydroamphotericin B(2-pyridylthio)ester;
N-(9-fluorenylmethoxycarbonyl)-16-decarboxy-16-hydroxy-methyl-3,5,8,9,11,15,35,2',4'-nona-N-triethylsilyl-13,14-anhydroamphotericin B;
N-trifluoroacetyl-3,5,8,9,11,15,35,2',4'-nona-O-triethylsilyl-13,14-anhydroamphotericin B;
N-trifluoroacetyl-3,5,8,9,11,15,35,2',4'-nona-O-triethylsilyl-13,14-anhydroamphotericin B (2-pyridylthio)ester;
N-trifluoroacetyl-16-benzoyl-16-decarboxy-3,5,8,9,11,15,35,2',4'-nona-O-triethylsilyl-13,14-anhydroamphotericin B; and
16-benzoyl-16-decarboxy-3,5,8,9,11,15,35,2',4'-nona-O-triethylsilyl-13,14-anhydroamphotericin B.

* * * * *